United States Patent
Melker et al.

(10) Patent No.: US 7,156,095 B2
(45) Date of Patent: *Jan. 2, 2007

(54) HYBRID MICROPROCESSOR CONTROLLED VENTILATOR UNIT

(75) Inventors: Richard J. Melker, Gainesville, FL (US); Michael J. Banner, Gainesville, FL (US); Samsun Lampotang, Gainesville, FL (US); Paul B. Blanch, Alachua, FL (US); Neil R. Euliano, Gainesville, FL (US); Ronald G. Carovano, Gainesville, FL (US)

(73) Assignee: University of Florida Research Foundation, Inc., Gainsville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/140,888

(22) Filed: May 9, 2002

(65) Prior Publication Data

US 2002/0185127 A1    Dec. 12, 2002

Related U.S. Application Data

(60) Division of application No. 09/457,709, filed on Dec. 10, 1999, now Pat. No. 6,976,487, which is a continuation of application No. 08/516,478, filed on Aug. 17, 1995, now Pat. No. 6,000,396.

(51) Int. Cl.
*A61M 16/00* (2006.01)
*A62B 7/00* (2006.01)

(52) U.S. Cl. ............... 128/204.18; 128/204.21; 128/204.23; 128/204.24; 128/204.26

(58) Field of Classification Search ......... 128/204.18, 128/204.21, 204.23, 200.24
See application file for complete search history.

(56) References Cited

U.S. PATENT DOCUMENTS

| 4,141,354 | A | * | 2/1979 | Ismach ............... 128/204.28 |
| 4,188,946 | A | | 2/1980 | Watson et al. |
| 4,393,869 | A | * | 7/1983 | Boyarsky et al. ...... 128/204.18 |
| 4,493,614 | A | * | 1/1985 | Chu et al. .............. 417/22 |
| 4,622,963 | A | * | 11/1986 | Ansite ................ 128/203.27 |
| D287,050 | S | | 12/1986 | Perkins et al. |
| 4,651,731 | A | | 3/1987 | Vicenzi et al. |
| 4,658,832 | A | | 4/1987 | Brugnoli |
| 4,713,888 | A | | 12/1987 | Broselow |
| 4,805,613 | A | | 2/1989 | Bird |
| 4,823,469 | A | | 4/1989 | Broselow |
| 4,823,787 | A | | 4/1989 | Adahan |
| 4,870,960 | A | | 10/1989 | Hradek |
| 4,905,688 | A | | 3/1990 | Vicenzi et al. |
| 4,941,469 | A | | 7/1990 | Adahan |

(Continued)

FOREIGN PATENT DOCUMENTS

EP    0615764    3/1994

OTHER PUBLICATIONS

*R. Melker, MD, "A Pediatric Gastric Tube Airway", Critical Care Medicine, vol. 9, No. 5, pp. 426-427.

(Continued)

*Primary Examiner*—Henry Bennett
*Assistant Examiner*—Nihir Patel
(74) *Attorney, Agent, or Firm*—Saliwanchik, Lloyd & Saliwanchik

(57) ABSTRACT

A method and apparatus for operating a ventilator in a primary electronic mode or in a back-up pneumatic mode during primary electronic mode failure. A method and apparatus for operating a ventilator in an advanced mode, having a number of ventilatory modes, or in a basic mode, having a limited number of ventilatory modes is also disclosed.

3 Claims, 16 Drawing Sheets

U.S. PATENT DOCUMENTS

| | | | | |
|---|---|---|---|---|
| 4,957,107 | A * | 9/1990 | Sipin | 128/204.21 |
| 4,990,894 | A | 2/1991 | Loescher et al. | |
| 5,042,470 | A * | 8/1991 | Kanesaka | 128/202.22 |
| 5,092,326 | A | 3/1992 | Winn et al. | |
| 5,094,235 | A | 3/1992 | Westenskow et al. | |
| 5,116,088 | A | 5/1992 | Bird | |
| 5,148,802 | A * | 9/1992 | Sanders et al. | 128/204.18 |
| 5,156,145 | A * | 10/1992 | Flood et al. | 128/201.24 |
| 5,183,038 | A * | 2/1993 | Hoffman et al. | 128/204.21 |
| 5,211,170 | A * | 5/1993 | Press | 128/204.18 |
| 5,211,171 | A | 5/1993 | Choromokos | |
| 5,239,995 | A * | 8/1993 | Estes et al. | 128/204.23 |
| 5,245,995 | A * | 9/1993 | Sullivan et al. | 128/204.23 |
| 5,303,698 | A | 4/1994 | Tobia et al. | |
| 5,303,699 | A * | 4/1994 | Bonassa et al. | 128/204.21 |
| 5,493,488 | A * | 2/1996 | Castle et al. | 700/42 |
| 5,503,145 | A * | 4/1996 | Clough | 128/204.22 |
| 5,535,738 | A * | 7/1996 | Estes et al. | 128/204.23 |
| 5,577,496 | A * | 11/1996 | Blackwood et al. | 128/201.25 |
| 5,598,838 | A * | 2/1997 | Servidio et al. | 128/204.23 |
| 5,884,622 | A * | 3/1999 | Younes | 128/204.21 |
| 5,931,162 | A * | 8/1999 | Christian | 128/204.23 |
| 6,000,396 | A * | 12/1999 | Melker et al. | 128/204.21 |
| 6,041,780 | A * | 3/2000 | Richard et al. | 128/204.18 |
| 6,105,575 | A * | 8/2000 | Estes et al. | 128/204.23 |
| 6,152,129 | A * | 11/2000 | Berthon-Jones | 128/200.24 |
| 6,240,919 | B1 * | 6/2001 | MacDonald et al. | 128/204.18 |
| 6,367,474 | B1 * | 4/2002 | Berthon-Jones et al. | 128/204.23 |
| 6,463,930 | B1 * | 10/2002 | Biondi et al. | 128/204.21 |
| 6,530,372 | B1 * | 3/2003 | Madaus et al. | 128/204.23 |
| 6,532,956 | B1 * | 3/2003 | Hill | 128/204.18 |
| 6,532,957 | B1 * | 3/2003 | Berthon-Jones | 128/204.21 |
| 6,575,163 | B1 * | 6/2003 | Berthon-Jones | 128/204.18 |
| 6,584,973 | B1 * | 7/2003 | Biondi et al. | 128/204.21 |
| 6,588,422 | B1 * | 7/2003 | Berthon-Jones et al. | 128/204.23 |
| 6,601,583 | B1 * | 8/2003 | Pessala et al. | 128/204.23 |
| 6,609,517 | B1 * | 8/2003 | Estes et al. | 128/204.23 |
| 6,622,726 | B1 * | 9/2003 | Du | 128/204.26 |
| 6,688,307 | B1 * | 2/2004 | Berthon-Jones | 128/204.21 |

OTHER PUBLICATIONS

*Joseph M. Civetta, MD, et al., Critical Care 2nd ed., chapter 108, pp. 1394-1416 (1992).

*A. Zapletal et al., "Lung Function in Children and Adolescents", Methods, Reference Values, H. Herzog Ed., Progress in Respiration Research, vol. 22, Karger 1987.

* cited by examiner

HYBRID MICROPROCESSOR CONTROLLED VENTILATOR UNIT

This is a divisional application based upon U.S. patent application Ser. No. 09/457,709, filed on Dec. 10, 1999, now U.S. Pat. No. 6,976,487 which is a continuation of U.S. patent application Ser. No. 08/516,478, filed Aug. 17, 1995 now U.S. Pat. No. 6,000,396, issued on Dec. 14, 1999, both of which are hereby incorporated in their entireties by reference.

FIELD OF THE INVENTION

The present invention relates to a ventilator unit. More particularly, the present invention relates to a hybrid microprocessor controlled ventilator unit. The ventilator of the present invention may be operated either in a basic mode, as a minimally featured transport ventilator unit, or in an advanced mode as a full featured ventilator for use in transport situations, in emergency situations or in ICU situations.

BACKGROUND OF THE INVENTION

Ventilation is the physiologic process of moving a gas into and out of the lungs and thereby delivering oxygen to organs of the body and excreting carbon dioxide. During spontaneous ventilation, i.e. unassisted breathing, negative (sub-atmospheric) pressure is created within the chest and gas moves into the lungs. In spontaneous ventilation exhalation is passive.

In the practice of medicine, there is often a need to substitute mechanical ventilatory support for the spontaneous breathing of a patient. This may be necessary during respiratory failure or when patients are placed under anesthesia.

Mechanical ventilatory support may be accomplished by displacing a known volume of gas into the lungs of the patient under positive pressure (any pressure greater than atmospheric pressure). Alternatively, mechanical ventilatory support may be accomplished by creating a negative pressure around the chest cavity to mimic spontaneous inhalation. While negative pressure (sub-ambient) is occasionally used for mechanical ventilatory support, positive pressure ventilation is far more common.

Attempts have been made to provide transport ventilation devices designed to provide positive pressure ventilation. These attempts have resulted in two categories of devices; (1) minimally featured transport ventilation devices designed for use by medical personnel having limited respiratory training, these devices operating in a limited number of ventilation modes, and (2) ventilators which have a large number of features, operate in a wide range of ventilation modes and which consequently are suited for use only by medical personnel with significant respiratory training. These attempts are described in a number of issued United States patents including the following:

U.S. Pat. No. 5,211,170 discloses a portable emergency respirator containing an electrically driven air compressor for generating air flow. The air compressor can be operated in one of three different modes to produce three different types of pneumatic outputs.

U.S. Pat. No. 4,941,469 and related U.S. Pat. No. 4,823,787 disclose portable ventilator units having electrically driven cyclically operated reciprocating pumps for providing pressurized air to a patient. The ventilators of these patents may be operated in a number of ventilator modes.

U.S. Pat. No. 4,905,688 discloses a pneumatically driven portable self contained ventilator/resuscitating device utilizing a solid state oxygen generator, such as a chlorate candle. The ventilator/resuscitator is designed for use by personnel with limited respiratory training and thus has limited features and ventilation modes.

U.S. Pat. No. 4,651,731 discloses a pneumatically driven portable self contained ventilator/resuscitating device utilizing a solid state oxygen generator, such as a chlorate candle. The ventilator/resuscitator has a number of adjustable features and various ventilator modes and is intended for operation by medical personnel with significant respiratory training.

These prior systems have many disadvantages. In particular, the minimally featured ventilators can maintain ventilation of seriously ill patients, however, they lack many of the advanced features found on the more sophisticated ventilators. These devices have limited utility in that they are suited only to short term ventilation such as would be necessary during transport situations.

In contrast, the more sophisticated ventilators are generally more costly, larger and require more training to operate than the minimally featured ventilators. As a result the more sophisticated ventilators are impractical for use in many environments such as aero-medical transport, in emergency departments, during intra-hospital transport and in hospitals of developing or third world countries.

In the prior devices which are microprocessor controlled or utilize electrically driven gas supplies, an electrical failure can result in an inoperative ventilator. Alternatively, the prior devices, which are pneumatically driven and controlled, lack many of the advanced safeties and features available through the use of modern microprocessor technology.

In addition, these prior devices require the initial parameters, such as tidal volume ($V_T$), ventilatory breathing frequency (f) and inspiratory flow rate ($V_i$) to be input by the health care provider. These values are generally determined based on the patients weight and age. In emergency situations the difficulty in accurately determining a patient's weight as well as errors in inputting the parameters can result in improper, even dangerous, ventilator settings. The prior art devices do not provide for safety mechanisms to prevent such occurrences.

SUMMARY OF THE INVENTION

The present invention relates to a hybrid microprocessor controlled ventilator.

In one aspect of the present invention a ventilator is provided having a ventilation flow rate control device and a controller for adjusting the ventilation flow rate control device. The controller can be operated in a first mode to adjust the ventilation flow rate control device to provide ventilation in one of a first set of ventilation modes or it can be operated in a second mode to adjust the ventilation flow rate control device to provide ventilation in one of a second set of ventilation modes.

In another aspect of the present invention a method of operating a ventilator is provided wherein data representing the body length of a patient to be ventilated is input into a control device, initial ventilation parameters are calculated based on the input body length data, and ventilation is then provided in accordance with the calculated initial ventilation parameters.

In another aspect of the present invention a ventilator is provided having a primary ventilator subsystem, a solenoid gas supply valve having a plurality of outputs (modes) and a back-up ventilator subsystem. The back-up ventilator has a pneumatically operated valve, a timing unit coupled to the pneumatically operated valve for opening the pneumatically operated valve at preselected intervals, and a flow rate control device connected to the pneumatically operated valve for receiving an output from the pneumatically operated valve. The solenoid gas supply valve provides a supply to the primary ventilator subsystem under a first set of operating conditions, and provides a supply to the back-up ventilator subsystem under a second set of operating conditions.

It is an object of the present invention to provide an inexpensive full featured ventilator unit having a "basic" and "advanced" mode that, in the basic mode, can be operated by health care providers having limited respiratory training and that, in the advanced mode, can be operated by skilled healthcare providers as a full featured ICU ventilator.

It is also an object of the present invention to provide a ventilator having an automated ventilation set-up feature for automatically setting the initial values of tidal volume ($V_T$), ventilatory breathing frequency (f) and inspiratory flow rate ($V_i$) based upon the patient's length.

It is a further object of the present invention to provide a ventilator having incorporated therein a parameter tracking, independent pneumatic back-up ventilator (BUV). In the event of electrical power failure or failure in the primary electronic ventilator, the ventilator will automatically operate in the back-up mode using solely pneumatic power and the ventilation parameters set prior to the failure.

It is a further object of the present invention to provide a ventilator having an electrical power-independent control system for maintaining continuous positive airway pressure (CPAP). This control system maintains the CPAP, at the level provided prior to electrical power failure, or primary electronic ventilation failure, during BUV operation.

It is a further object of the present invention to provide a ventilator having a BUV lockout system. The lockout system prevents the BUV from operating, using previously set ventilation parameters, during initial power-up of the ventilator unit.

It is a further object of the present invention to provide a ventilator having a mechanism for adaptively setting the rate of airway pressure rise during pressure support ventilation (PSV). This mechanism will allow the rate of rise, that best minimizes work of breathing for the patient, to be automatically set shortly after the PSV mode is activated.

It is a further object to the present invention to provide a ventilator having a mechanism for conserving gas during periods when the patient is disconnected from the ventilator.

It is a further object to the present invention to provide a ventilator which automatically compensates for increases and decreases in atmospheric (ambient) pressure. Changes in pressure can result, for example, from the use of the ventilator at increased altitudes, such as in aero-medical transport, or from the use of the ventilator in hyperbaric chambers.

It is a further object to the present invention to provide a ventilator having a mechanism for automatically setting ventilation parameter limits based on body length of the patient and which thereby prevents unskilled users from setting ventilation parameters which may be dangerous to the patient.

It is a further object to the present invention to provide a ventilator having a mechanism for setting ventilator alarms based on patient's body length.

Additional objects and advantages of the invention will be set forth in part in the description which follows, and in part will be obvious from the description, or may be learned by practice of the invention. The objects and advantages of the invention will be obtained by means of instrumentalities in combinations particularly pointed out in the appended claims.

BRIEF DESCRIPTION OF THE DRAWINGS

The accompanying drawings illustrate a complete embodiment of the invention according to the best modes so far devised for the practical application of the principles thereof, and in which.

DETAILED DESCRIPTION OF A PREFERRED EMBODIMENT

Figure 1:
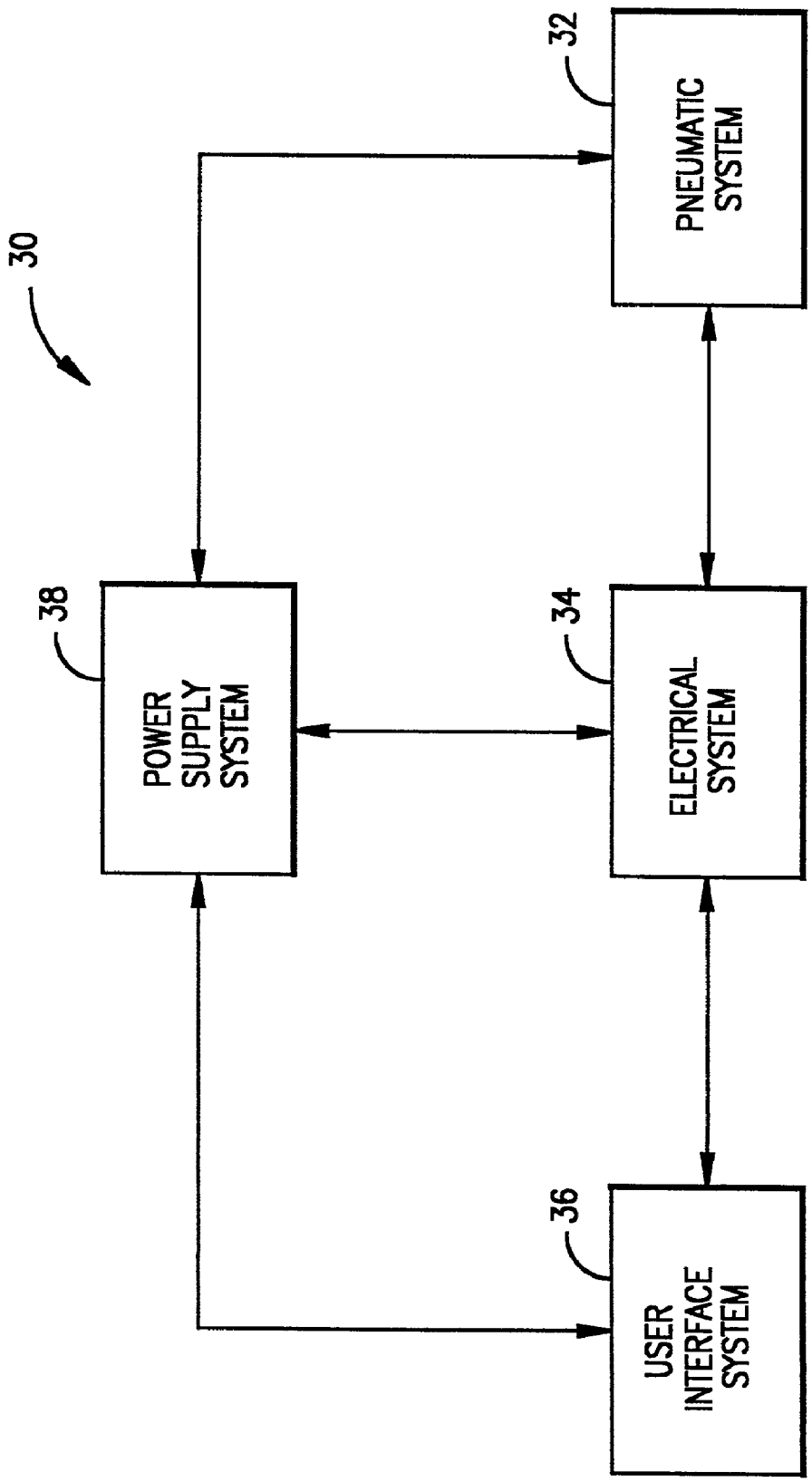
FIG. 1 is a block diagram illustration of a ventilator in accordance with a preferred embodiment of the present invention.

Referring now to the figures, wherein like numerals indicate like elements, in FIG. 1 there is shown a block diagram illustration of a ventilator, generally designated by reference number 30, in accordance with a preferred embodiment of the present invention. The ventilator includes a pneumatic system 32, an electrical system 34, a user interface system 36 and a power supply system 38. Each of these systems will be set forth and described below.

Figure 2:
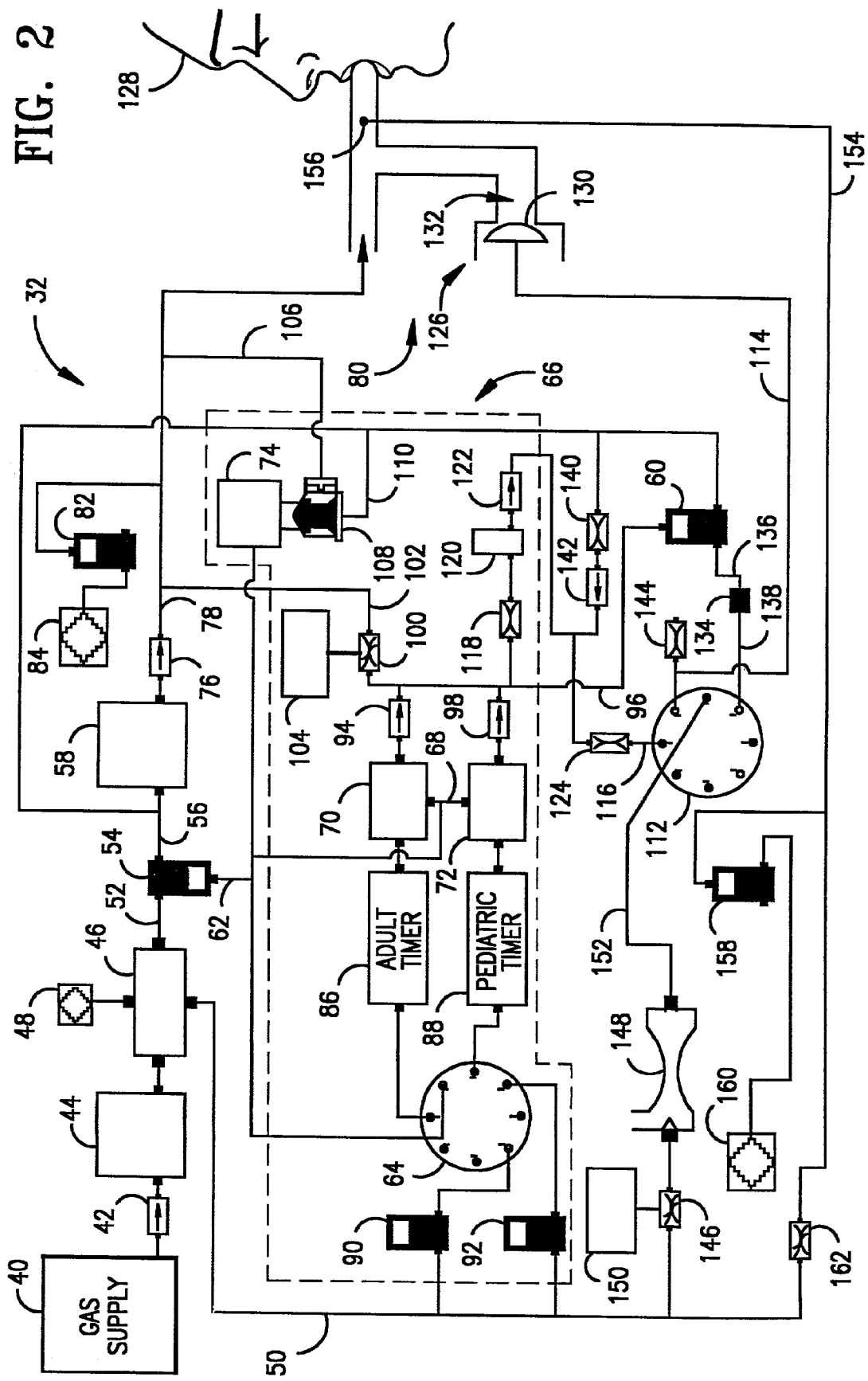
FIG. 2 is a schematic illustration of the pneumatic system of the ventilator of FIG. 1.

In FIG. 2 there is shown the pneumatic system 32 of the ventilator of FIG. 1. The pneumatic system 32 includes a primary ventilator sub-system and a back-up ventilator sub-system. Each of these sub-systems will be described below.

In operation, gas is supplied to the pneumatic system 32, from a gas supply 40, at the input of a one way check valve 42. The gas may be air, pure oxygen or a mixture thereof. The gas supply 40 provides the gas at a pressure at least sufficient to force the gas through the system, to operate the pneumatic portion of the system, and to supply gas to the patient. The check valve 42 permit the flow of gas only into the pneumatic system 32 and not back to the gas supply 40.

It should be understood that modification of the ventilator described herein may be made in order to supply other desired gases. Such modifications will be readily apparent, from the description set forth herein, to one of ordinary skill in the design of ventilators.

The gas supply passes through the check valve 42 and is received by a precision regulator 44 which regulates the input supply pressure down to a stable level. The regulator 44 is required since input supplies vary from location to location within a hospital environment. In the embodiment of FIG. 2 the regulator 44 operates to regulate the gas pressure exiting the regulator to about forty pounds per square inch gauge (psig).

The regulated gas supply passes then to a plenum 46 which stabilizes the pressure and flow rate of gas. Variations in pressure and flow rate could affect the operation of the ventilator 30 and could be detrimental to the patient. The volume of the plenum 46 should be selected to be large enough to ensure dampening of pressure fluctuations and ensure that there is enough gas-volume to meet the peak expected flow rate demand, but should be as small as feasible to reduce space requirements. In the embodiment of FIG. 2 the plenum 46 volume is approximately one liter.

A tap is provided in the plenum 46 so that a pressure transducer 48 can be connected. The pressure transducer provides an input signal to the ventilation control board 222, FIG. 12, indicating the pressure in the plenum 46. If the pressure in the plenum 46 is too low a microprocessor on the ventilation control board 222, FIG. 12 sends a signal to the user interface control board 218 directing that an alarm 238 be sounded to alert the user that there is a problem up stream of the plenum 46. Similarly, if the pressure is too high an alarm will sound.

The plenum 46 has two separate output lines 50, 52. There is a constant supply of gas to each of the output lines 50, 52. The first output line 50 provides gas supply for BUV operation, CPAP operation and provides a supply for use in airway pressure sensing. Each of these features will be described in greater detail below. The second output line 52 of the plenum 46 provides gas to a solenoid-driven three-way valve 54.

When energized the three-way valve 54 supplies gas to output line 56 which in turn provides an input to a proportional flow control valve (PFCV) 58 and to a three-way solenoid-driven valve 60. When the three-way valve 54 is not energized, gas is supplied to a second output line 62. The second output line 62 supplies gas to a selector valve 64 of the BUV sub-system, depicted within the dotted lines in FIG. 2 and denoted generally by reference numeral 66, the gas supply line 68 for switches 70 and 72 and to a demand valve 74.

Figure 12:
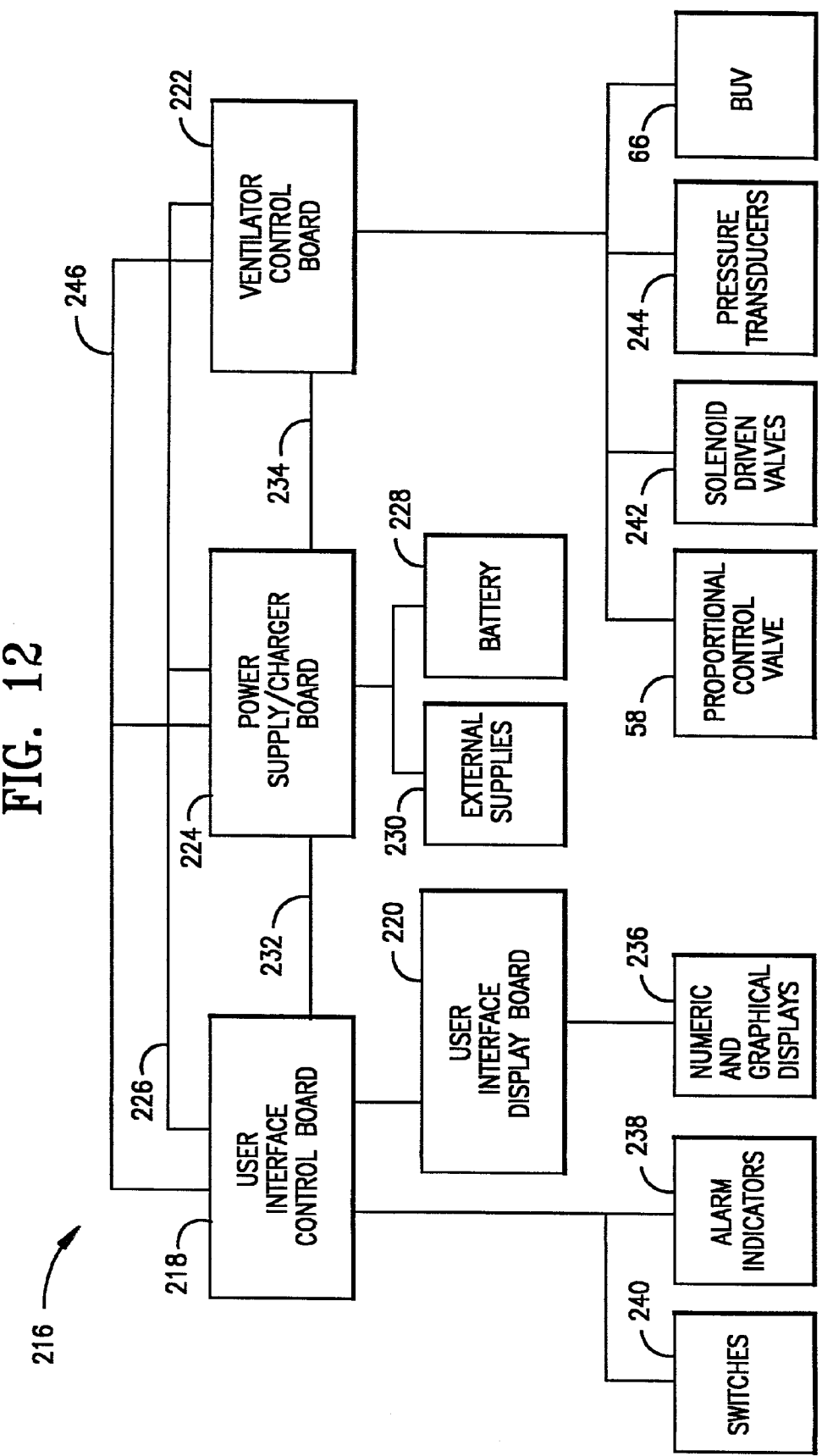
FIG. 12 is a block diagram illustration of the electrical system of the ventilator of FIG. 1.

The PFCV 58 is controlled by a microprocessor, on the ventilator control board 222, FIG. 12. The PFCV 58 is designed by Technocraft Inc., Palm Bay, Fla.

Gas flows out from the PFCV 58 through a one way valve 76 to a primary gas output line 78. The primary gas output line 78 provides gas to the patient breathing circuit 80. The valve 76 prevents the flow of gas back into the PFCV 58 during operation of the BUV.

A tap in the primary gas output line 78 allows for the connection of a solenoid-driven three-way valve 82. A pressure sensor 84 is connected to the normally open output of the valve 82. The sensor 84 provides an input signal to the ventilator control board 222, FIG. 12, which is used to determine pressure at this site.

The valve 82 is used to compensate for drift in the pressure sensor 84. In the embodiment of the pneumatic system of FIG. 2, the pressure sensor 84 is zeroed to atmospheric pressure before each use of the ventilator and periodically during operation.

In the case of microprocessor or electrical failure, the three-way valve 54 will not be energized and thus will return to its normally open state and supply gas to output line 62. The ventilator will then operate in the BUV mode.

In BUV mode output line 62 provides gas to selector valve 64. The selector valve 64 will have been set during primary ventilator mode operation to provide gas to the adult timer unit 86 or to the pediatric timer unit 88.

The process by which the selector valve 64 is set is as follows, during primary electronic ventilation if the ventilator operation has been set to ventilate an adult the solenoid-driven three-way valve 90 will be energized momentarily. Gas is then supplied, through valve 90, from the output line 50 to the selector valve 64. This gas supply sets the selector valve 64 to connect the output line 62 to the adult timer 86.

Alternatively, if the ventilator was set to ventilate a pediatric patient a solenoid driven three-way valve 92 will be energized momentarily. Gas is then supplied, through valve 92, from the output line 50 to the selector valve 64. This gas supply will set the selector valve 64 to connect the output line 62 to the pediatric timer 88.

Once set by momentarily energizing one of the valves 90, 92 the selector valve 64 will remain in its set position until reset by energizing the alternate valve 92, 90. In the preferred embodiment the selector valve 64 is a CLIPPARD 302 selector valve.

The adult timer unit 86 and pediatric timer unit 88 are pneumatically driven timers. When in back-up mode the gas supplied through the selector valve 64 drives either the adult timer unit 86 or pediatric timer unit 88.

When ventilating an adult, at intervals determined by the timer unit 86, gas is supplied to open a valve 70. When the valve 70 is open, gas will flow from a supply line 68, which is supplied by output line 62, through the valve 70 and into a check valve 94 where it is then provided to a supply line 96.

Alternatively, if ventilating a pediatric patient, during back-up ventilation, the pediatric timer 88 will supply gas at selected intervals to a valve 72 allowing gas to flow from a supply line 68 to a check valve 98 where it is then provided to a supply line 96.

The gas supply line 96 provides gas to a needle valve 100 and to the valve 60. The needle valve 100 determines the flow rate of gas to the back-up ventilator output line 102 which is then supplied to the breathing circuit 80 via the primary gas output line 78. The needle valve 100 is adjusted during the primary ventilation mode and then, if the ventilator is forced to operate in back-up ventilation mode, will remain at the last setting prior to back-up ventilation mode operation.

The needle valve 100 is adjusted as follows. When the ventilator is operating in primary ventilation mode a stepper motor 104, which is controlled by the microprocessor in the ventilator control board 222, FIG. 12, adjusts the needle valve 100. The initial setting of the needle valve 100 is based upon an algorithm utilizing the patient's length to determine tidal volume. This algorithm is explained in more detail below.

The demand valve 74 is provided with a patient demand valve interface 108. When the ventilator is operating in the primary ventilation mode, gas supplied on supply line 110 maintains the demand valve 74 in the closed position thus preventing the operation of the demand valve 74. When in the back-up mode, no gas is supplied via supply lines 56, 110 and thus the demand valve 74 may operate.

While operating in the back-up mode the patient's demand for gas may exceed that provided by the ventilator. When the patient's demand exceeds the supply of gas from the back-up ventilator sub-system 66, demand valve 74 will open and allow gas to flow directly from the output supply line 62 to the patient via a separate supply line 106.

What will now be described is the operation of the exhalation valve charging subsystem, first while operating in back-up ventilation mode and then in primary ventilation mode.

As described above, while operating in back-up mode, gas is supplied at selected intervals, on supply line 96, to the normally open port of solenoid-driven three-way valve 60. While gas is being supplied on line 96 it will pass through the valve 60 to a diverter valve 112 causing the diverter valve 112 to connect the exhalation valve charging line 114 to diverter valve supply line 116. In the preferred embodiment the diverter valve 112 is a CLIPPARD 305 valve.

The gas supplied by the back-up ventilator sub-system 66 on to supply line 96, is reduced in pressure by a needle valve 118 and regulated by a precision regulator 120. During normal ventilator operation, check valve 122 is provided in the circuit to prevent the back flow of gas on to supply line 96. The gas is reduced in pressure a second time by a needle valve 124 and provided through the diverter valve supply line 116 to the diverter valve 112 where it is diverted to the exhalation valve charging line 114.

While gas is being provided to the exhalation valve charging line 114 from supply line 116, an exhalation valve 126, is maintained closed ensuring the flow of gas on the primary supply line 78 goes to the patient.

The operation of the exhalation valve 126 will now be explained. During inhalation the PFCV 58 provides gas flow to the primary gas supply line 78 and thus to the patient 128. While gas is being supplied to the patient 128, gas is also supplied to the exhalation valve charging line 114 inflating a bladder 130, closing off the exhalation port 132 of the exhalation valve 126.

In the BUV mode the gas supplied on supply line 96 both provides the gas supply to the patient 128 and drives the diverter valve 112 to supply gas to the exhalation charging line 114, thus, these two functions are pneumatically tied together.

In the primary ventilation mode, the microprocessor of the ventilator control board 222 controls both the proportional flow rate control valve 58 and the solenoid driven valve 60. The microprocessor closes the exhalation port 132 by activating valve 60 when gas is being supplied on primary gas supply line 78.

When exhalation is desired the supply to the exhalation valve charging line 114 ceases, either because the microprocessor of the ventilator control board 222 turns off the valve 60 or because the back-up ventilator subsystem 66 ceases to supply gas on supply line 96. When the supply to the exhalation valve charging line 114 ceases the bladder 130 deflates and allows the patient 128 to exhale out of the exhalation port 132.

When the gas supply on supply line 96 ceases, the diverter valve 112 will switch, disconnecting supply line 116 from the exhalation valve charging line 114. A quick release valve 134 is provided to allow the diverter valve 112 to switch rapidly. When the pressure at the input supply line 136 of the quick release valve 134 is greater than that at the output supply line 138 the valve 134 remains closed. When the pressure at the input supply line 136 falls slightly below that at the output, i.e. when gas flow rate on supply line 96 ceases, the quick release valve 134 opens, quickly purging the gas in supply line 138, and allowing the diverter valve 112 to switch.

During primary ventilation mode operation, valve 60 is supplied with gas via supply line 56. When the microprocessor of the ventilator control board 222, FIG. 12, energizes the valve 60, gas flows into the diverter valve 112 and the circuit operates as described above with respect to back-up mode operation. The gas supplied at supply line 116 is provided now through needle valve 140. A check valve 142 is provided to prevent gas from flowing back onto supply line 56 during BUV operation.

An orifice 144, connected to a tap on the exhalation valve charging line 114, is shunted to open air. This orifice 144 provides a constant bleed for pressure in the exhalation valve charging line 114 when that pressure exceeds atmospheric pressure.

During spontaneous ventilation, the lungs do not completely deflate upon exhalation as a result of a fluid coating on the lungs. Injury or illness may sometimes impede a patient's ability to generate this coating and thus it may be necessary or desired to provide continuous positive airway pressure (CPAP) to prevent the complete deflation of the lungs.

In the ventilator of the present invention CPAP is provided during primary and back-up ventilation mode operation on the exhalation valve charging line 114. When CPAP is desired, gas is supplied on output supply line 50 through needle valve 146 to an integral venturi (also known as ejector or jet pump) 148. During primary ventilation mode a stepper motor 150, controlled by the microprocessor in the ventilator control board 222, FIG. 12, adjusts the needle valve 146 to control the gas supply to the integral venturi 148.

The gas supply to the integral venturi 148 from the needle valve 146 causes outside air to flow into the integral venturi 148 to supply line 152. The supply line 152, which is connected to the exhalation valve charging line 114 during exhalation, provides a continuous supply to the bladder 130 at a preset CPAP level. Thus, while CPAP is provided, the patient 128 is permitted to exhale only to the preset CPAP level.

If there is a microprocessor or electrical failure, and thus the ventilator switches over to back-up mode, the needle valve 146 will remain in the setting last entered before the ventilator switched over to back-up mode.

There is also provided in the pneumatic system an airway pressure sensing line 154. The pressure sensing line 154 is connected to the breathing circuit 80 at a tap 156. The pressure sensing line 154 also contains a tap which allows for the connection of a three-way solenoid-driven valve 158. A pressure sensor 160, which is connected to the common output of the solenoid-driven three-way valve 158, is used to determine the pressure at the patient's airway.

The valve 158 is used to compensate for drift in the pressure sensor 160. In the embodiment of the pneumatic system of FIG. 2, the pressure sensor 160 is zeroed to atmospheric pressure before each use of the ventilator and periodically during operation.

The ventilator of the present invention is provided with a gas saving feature to prevent loss of gas during disconnect of the breathing circuit 80 during CPAP, PCV and/or PSV operation. This feature is of particular utility while the ventilator is operating in a transport environment where gas supply is limited. During periods when the breathing circuit 80 is disconnected from the ventilator, such as during airway suctioning, a substantial waste of gas can occur as the ventilator increases gas flow rate to try and maintain the CPAP pressure.

In the ventilator of the present invention, when a patient becomes disconnected the airway pressure drops due to disconnect, the change in pressure is sensed by the pressure transducer 160 and reported to the microprocessor of the ventilator control board. In response to this pressure change the microprocessor instructs the user interface board 218 to sound an alarm 238 and operates the solenoid driven valve 60 and PFCV 58 to deliver short bursts of gas until a rise in pressure occurs during one of the bursts. This feature markedly increases the life of compressed gas cylinders which are used during transport.

The airway pressure sensing line 154 is supplied with a small flow rate of gas from supply line 50 through a needle valve 162. This purge flow rate is provided to keep obstructions out of the airway pressure sensing line 154.

In the preferred embodiment of the pneumatic system of FIG. 2 the PFCV 58 can be operated to provide an output gas supply in one of nine ventilatory modes. Each of these ventilatory modes are described below with reference to FIGS. 3 through 11.

Figure 3:
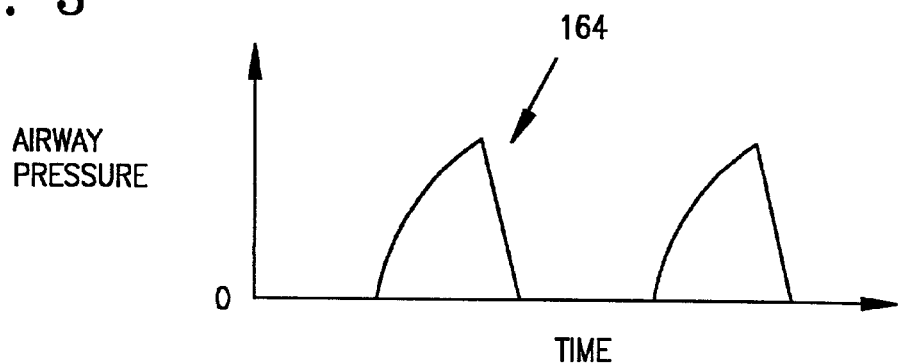
FIG. 3 is a graph depicting airway pressure as a function of time in the ventilator of FIG. 1 in the controlled mechanical ventilation (CMV) mode.

The first ventilatory mode, depicted in FIG. 3, is controlled mechanical ventilation (CMV). In the CMV mode, the ventilator operates at a preselected ventilator rate, tidal volume, and inspiratory flow rate, which are independent of the spontaneous effort on the part of the patient. A peak inflation pressure 164 is generated which varies inversely with compliance and directly with resistance.

Figure 4:
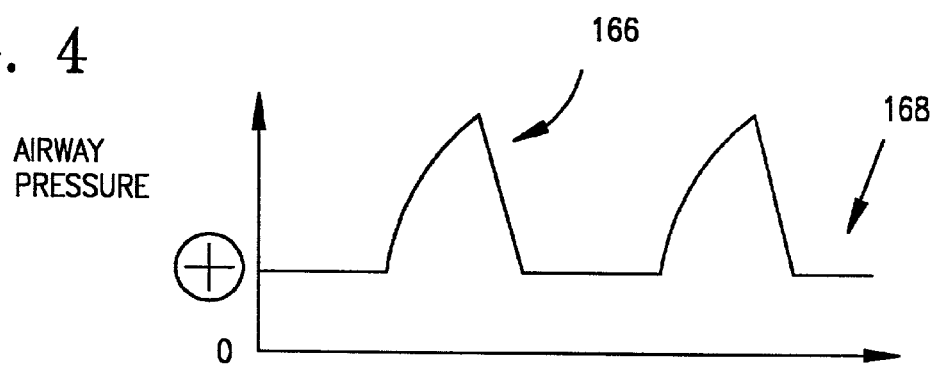
FIG. 4 is a graph depicting airway pressure as a function of time in the ventilator of FIG. 1 in the controlled mechanical ventilation with positive end expiratory pressure (CMV-PEEP) mode.

The second ventilatory mode, depicted in FIG. 4, is controlled mechanical ventilation with positive end expiratory pressure (CMV-PEEP). In the CMV-PEEP mode the ventilator generates a positive pressure breath at a peak inflation pressure 166 followed by a fall in airway pressure to a previously selected positive pressure plateau 168; airway pressure does not return to zero.

Figure 5:
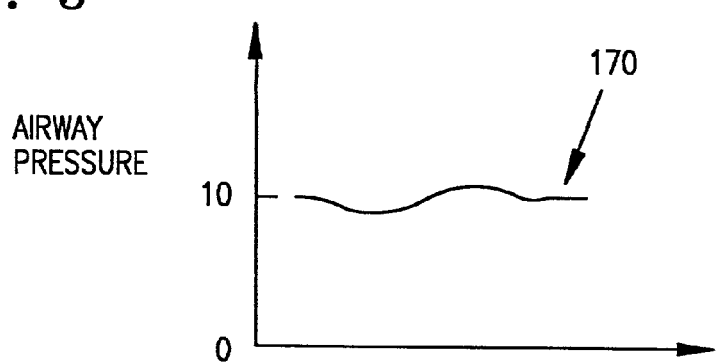
FIG. 5 is a graph depicting airway pressure as a function of time in the ventilator of FIG. 1 in the continuous positive airway pressure (CPAP) mode.

The third ventilatory mode, depicted in FIG. 5, is continuous positive airway pressure (CPAP). In the CPAP mode a positive airway pressure 170 is maintained continuously during spontaneous ventilation. In this mode the patient is supported not mechanically ventilated.

Figure 6:
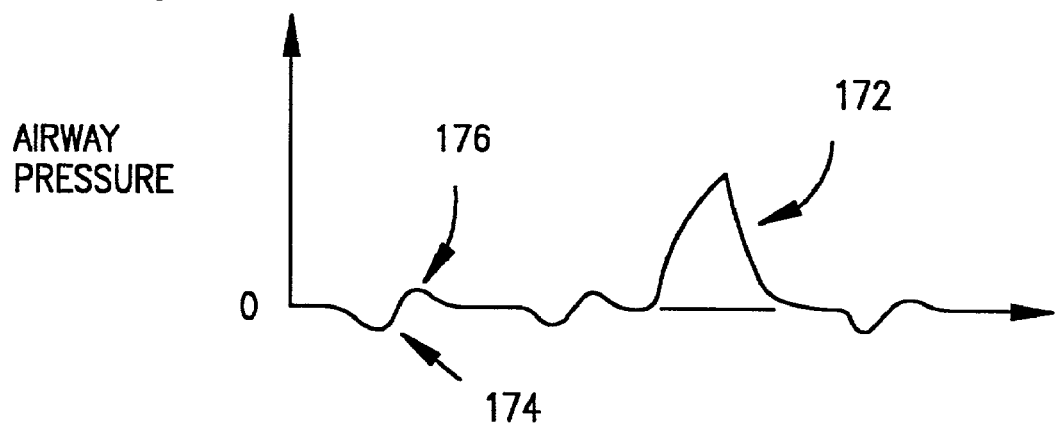
FIG. 6 is a graph depicting airway pressure as a function of time in the ventilator of FIG. 1 in the synchronized intermittent mandatory ventilation (SIMV) mode.

The fourth ventilatory mode, depicted in FIG. 6, is synchronized intermittent mandatory ventilation (SIMV). In the SIMV mode the patient is permitted to breathe spontaneously as desired, mechanical inflation is provided at preselected intervals. The SIMV rate is the ventilator rate. Between SIMV breaths 172 the patient inhales 174 and exhales 176 spontaneously from the ventilator's PFCV 58.

Figure 7:
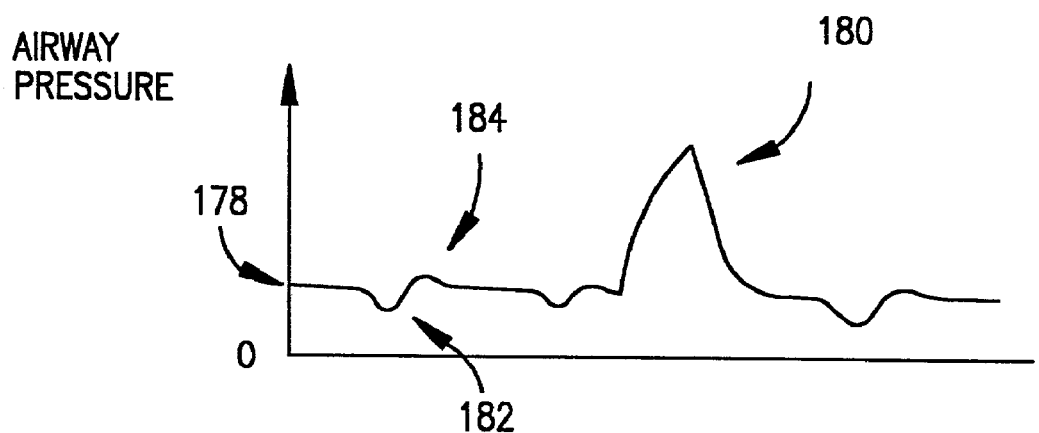
FIG. 7 is a graph depicting airway pressure as a function of time in the ventilator of FIG. 1 in the synchronized intermittent mandatory ventilation with continuous positive airway pressure (SIMV-CPAP) mode.

The fifth ventilatory mode, depicted in FIG. 7, is synchronized intermittent mandatory ventilation with continuous positive airway pressure (SIMV-CPAP). In the SIMV-CPAP mode, the patient is allowed to breath spontaneously as desired on a preselected level of CPAP 178. Between SIMV breaths 180 the patient inhales 182 and exhales 184 spontaneously from the ventilator's PFCV 58. In this mode SIMV breaths 180 are delivered at preset intervals.

Figure 8:
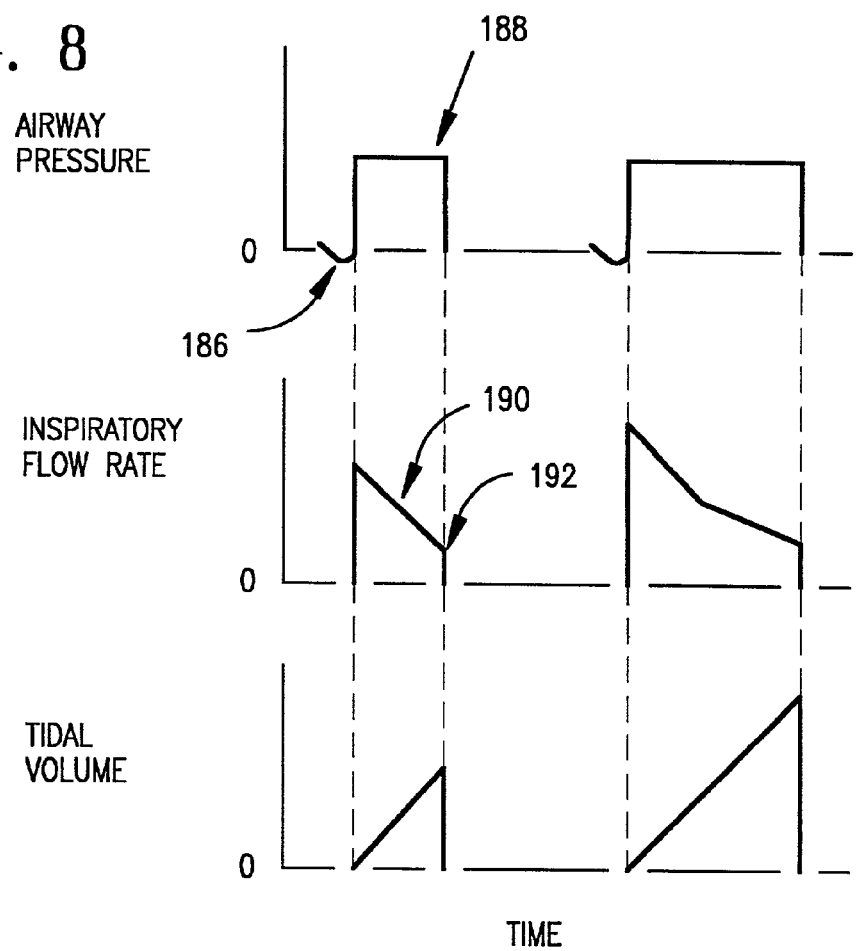
FIG. 8 is a graph depicting airway pressure, flow rate and tidal volume in the ventilator of FIG. 1 in the pressure support ventilation (PSV) mode.

The sixth ventilatory mode, depicted in FIG. 8, is pressure support ventilation (PSV). In the PSV mode, the ventilator is patient triggered "on" 186 and continues in the inhalation phase to a preselected positive pressure target. As long as the patient's effort is maintained, the preselected airway pressure remains constant 188, with a variable flow rate of gas 190 from the ventilator. Inhalation cycles "off" when the patient's inspiratory flow rate decreases to a predetermined percentage 192 of the initial peak mechanical inspiratory flow rate. The ventilator, thus, is flow rate cycled, following which passive exhalation occurs. With PSV the peak inspiratory flow rate, flow rate wave form, tidal volume, and airway pressure contour depend on the patient's breathing pattern. Tidal volume is determined by the level of PSV the patients inspiratory effort, total compliance, and total resistance.

Figure 9:
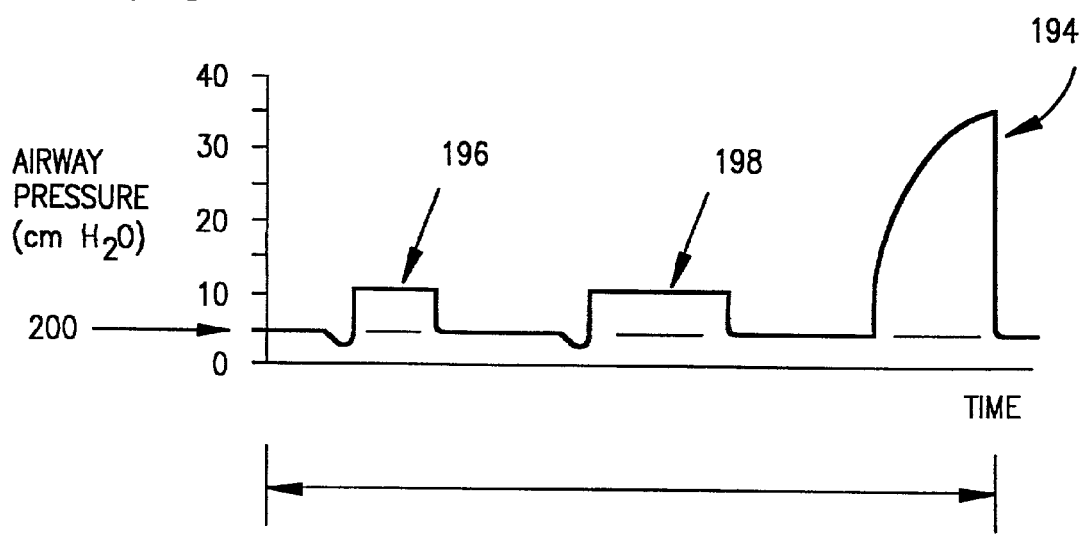
FIG. 9 is a graph depicting airway pressure as a function of time in the ventilator of FIG. 1 in the synchronized intermittent mandatory ventilation with continuous positive airway pressure and pressure support ventilation (SIMV-CPAP-PSV) mode.

The seventh ventilatory mode, depicted in FIG. 9, is synchronized intermittent mandatory ventilation with continuous positive airway pressure and pressure support ventilation (SIMV-CPAP-PSV). In the SIMV-CPAP-PSV mode, SIMV breaths 194 are provided during regular preset intervals. In between SIMV breaths 194, the patient receives PSV 196, 198 during spontaneously initiated breaths. During exhalation of SIMV breaths and PSV breaths, airway pressure decreases to a preselected CPAP level 200.

Figure 10:
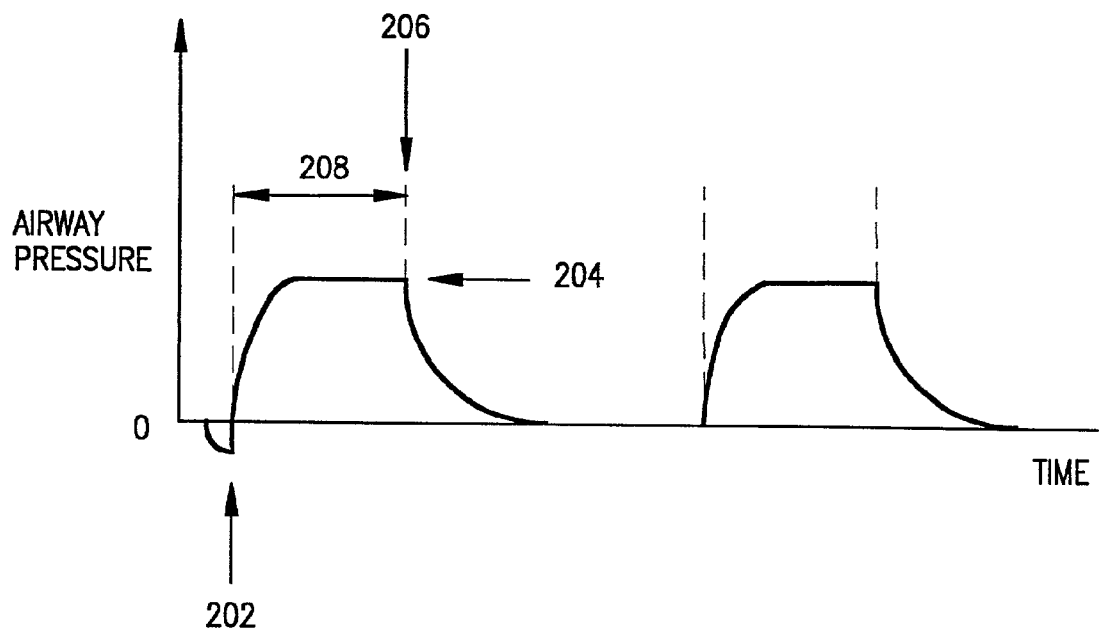
FIG. 10 is a graph depicting airway pressure as a function of time in the ventilator of FIG. 1 in the pressure controlled ventilation (PCV) mode.

The eighth ventilatory mode, depicted in FIG. 10, is pressure controlled ventilation (PCV). In the PCV mode, the ventilator is patient-triggered, or time-initiated, "on" 202, whichever occurs first, and continues in the inhalation phase to a preselected positive pressure limit 204. As long as the patient's effort is maintained, the preselected airway pressure remains constant 204, with a variable flow rate of gas from the ventilator. Inhalation cycles "off" 206 when the preselected inspiratory time 208 elapses. The ventilator, thus, is time cycled, following which passive exhalation occurs. With PCV the peak inspiratory flow rate, flow rate wave form, tidal volume, and airway pressure contour depend on the patient's breathing pattern. Tidal volume is determined by the level of PCV, the patient's inspiratory effort, total compliance, and total resistance.

Figure 11:
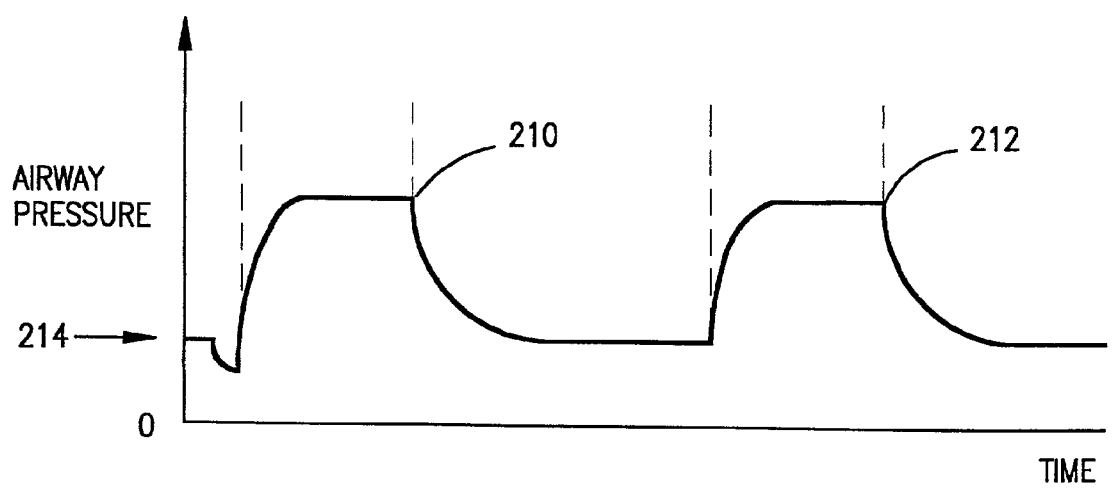
FIG. 11 is a graph depicting airway pressure as a function of time in the ventilation of FIG. 1 in the synchronized intermittent mandatory ventilation with continuous positive airway pressure and pressure controlled ventilation (SIMV-CPAP-PCV) mode.

The ninth ventilatory mode, depicted in FIG. 11, is pressure controlled ventilation combined with continuous positive airway pressure (PCV-CPAP). In the PCV-CPAP mode, positive pressure breaths 210, 212 are provided in the PCV mode as described above. During exhalation of the PCV breaths, airway pressure decreases to the preselected CPAP level 214.

In the ventilator of the embodiment of FIG. 1 several of the modes described above may be disabled so that the ventilator operates as a minimally featured transport ventilator. In particular, in the basic mode the ventilator will operate only in the SIMV-CPAP mode. In this mode, an upper limit for CPAP is provided which is substantially below the CPAP level ordinarily allowable. In the embodiment of the ventilator of FIG. 1, the CPAP level can be adjusted to provide a positive pressure in the range of 0 to 5 centimeters of water ($cmH_2O$)

In the advanced mode, ventilation can be provided in each of the nine modes described above. The upper limit on CPAP in the advanced mode can be set substantially above that permitted in the basic mode. In the embodiment of the ventilator of FIG. 1, CPAP can be adjusted to provide a positive pressure in the range of 0 to 30 $cmH_2O$.

The electrical system 216, FIG. 12, of the ventilator device of the embodiment of FIG. 1 consists of a user interface system, power supply system and ventilator control system.

The user interface system includes the user interface control board 218, user interface display board 220 containing LCD drivers, alphanumeric LCD displays 236, alarm indicators 238, switches 240 and a multi-purpose dial.

The power supply system includes a power supply and battery charger board 224 supplies power over line 226 for all the power requirements of the electronics and electrically controlled pneumatics of the ventilator. The power supply, is capable of running from a battery 228 or from AC or DC external supplies 230. The power supply system must be capable of operating over a wide range of AC voltage supplies available worldwide.

The ventilator control board 222 controls all operational logic of the ventilator. As such the ventilator control board 222 controls the operation of the proportional flow rate control valve 58, the solenoid driven valves 54, 60, 82, 90, 92 and 158 (collectively 242, FIG. 12), the pressure transducers 48, 84 and 160 (collectively 244, FIG. 12) and the back-up ventilator 66 settings.

The electrical system 216 of the ventilator communicates over watchdog/reset lines 232, 234, with the power supply and charger board 224 to provide a common Watchdog control circuit. The power supply board 224 contains a microprocessor that monitors the power supply levels and verifies that the user interface control board 218 and ventilator control board 222 are properly resetting the watchdog timer. If the power supplies get out of tolerance or if either the ventilator control board 222 or user interface control board 218 do not reset the watchdog before the time-out interval, the microprocessor of the power supply and charger board 224 will cut the power to the electrical system 216 and switch to the back-up ventilation mode.

Figure 13:
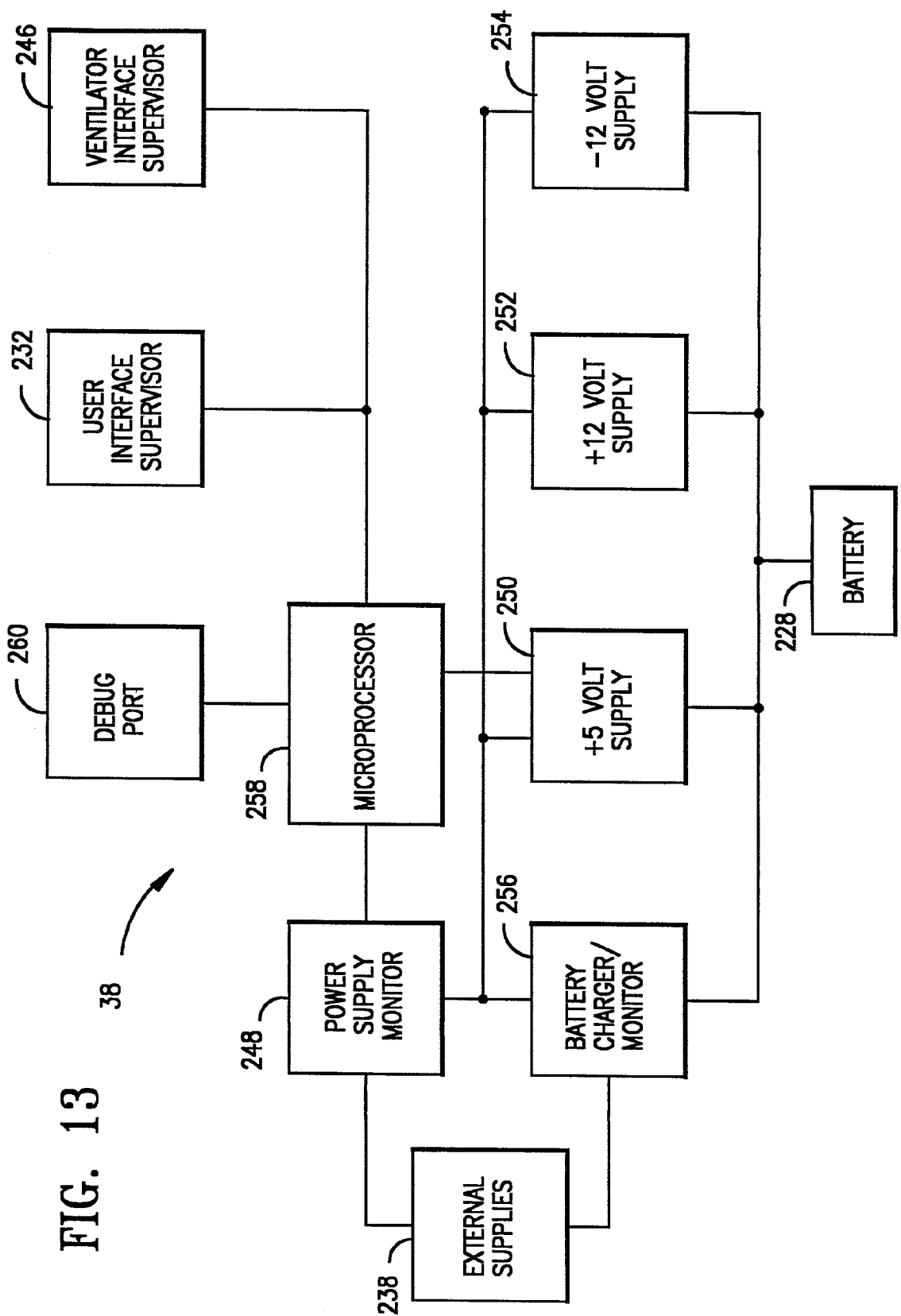
FIG. 13 is a block diagram illustration of the power supply system of the ventilator of FIG. 1.

The power supply subsystem 38, FIG. 13, contains a power supply monitor 248 which monitors the voltage, current and temperature of the battery 228 and the voltages of the five volt supply 250, the positive twelve volt supply 252 and negative twelve volt supply 254 and provides status indicators if the battery 228 or any of the DC outputs 250, 252, 254 falls outside normal tolerances.

A battery charger 256 charges the battery 228 and runs the ventilator simultaneously. The battery charger 256 also contains a monitor which monitors the battery 228 and provides signals to the microprocessor 258 indicating the remaining capacity of the battery.

The power supply and charger board 224 contains a debug port 260 for use in servicing the power supply sub-system 38.

Figure 14:
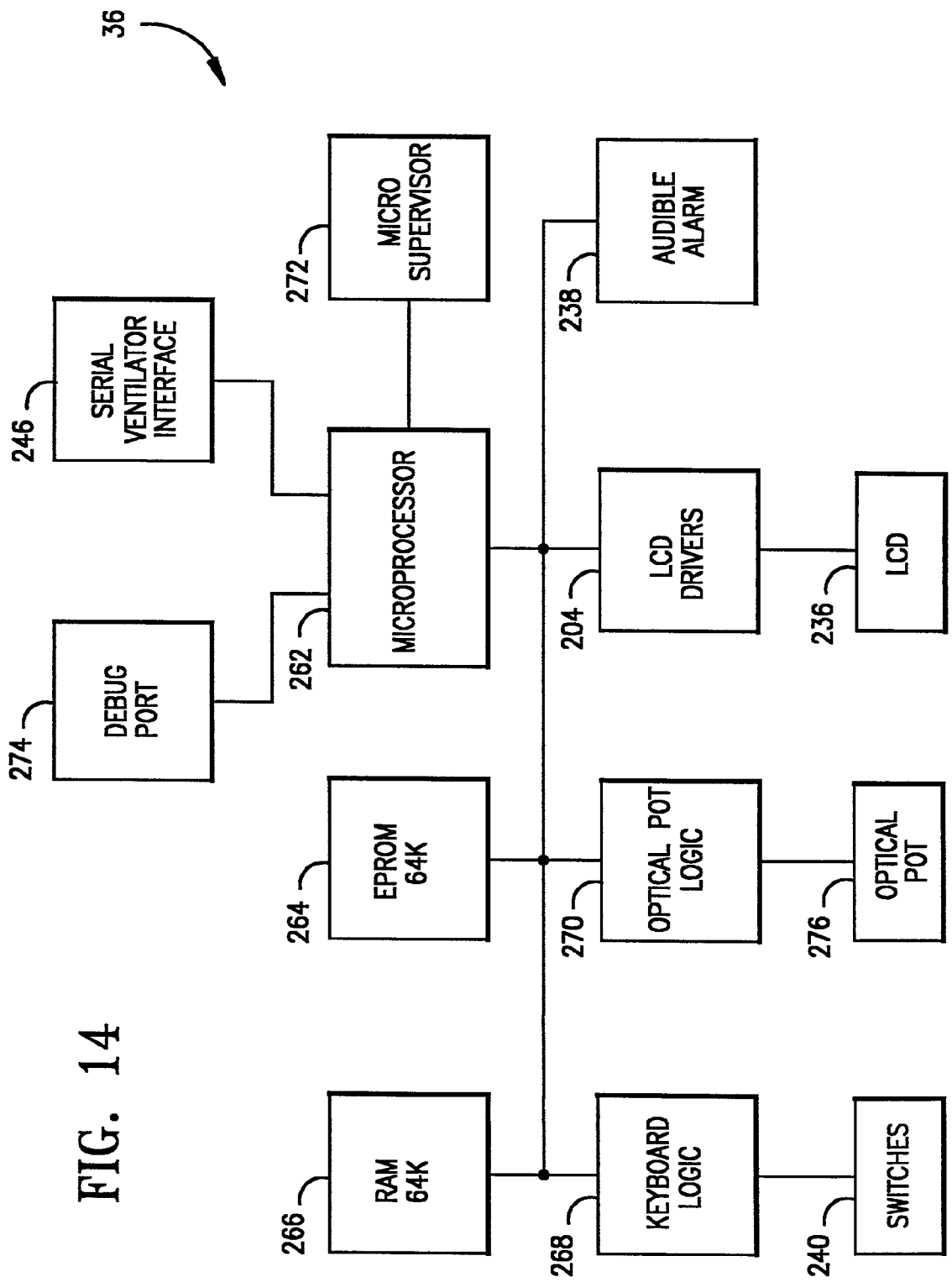
FIG. 14 is a block diagram illustration of the user interface system of the ventilator of FIG. 1.

The user interface system 36, FIG. 14, includes; a microprocessor 262, an EPROM 264, a RAM 266, a keyboard logic device 268, an optical potentiometer logic device 270, a micro supervisor 272, a debug terminal 274 and a multi-purpose dial 276.

The microprocessor of the user interface control board 218 communicates with the ventilator control board 222 over a serial multiprocessor communication line 246. Error detection of received information is provided on each control board using, for example, a cyclical redundancy code. A simple ACK/NAK protocol can be used to handle retransmission of bad data blocks.

The user interface display board 220, FIG. 12, controls the display of the current ventilator settings, messages, alarms and allows the user to vary these settings. In the embodiment of FIG. 1, individual numeric LCD displays 236 are provided for tidal volume, rate, flow rate, sensitivity, CPAP, PSV/PCV, length, PIP, high pressure alarm, and low pressure alarm. Inspiratory time and Inspiratory-Expiratory (I:E) ratio share a common display.

The audible alarms provided in the ventilator of the embodiment of FIG. 1 include apnea, high pressure, low pressure, disconnect, pressure transducer failure, and I:E ratio warning.

The user interface control board 218, FIG. 12, contains a debug terminal 274 for use in servicing the user interface system subsystem 36.

The user interface control board 218 also contains algorithms for setting initial parameters for tidal volume, rate, and I:E ratio based upon the length of the patient. In addition the user interface control board 218 automatically sets ventilatory parameter limits, PSV volume limits and alarms based upon the length of the patient.

Traditionally, the tidal volume setting on a ventilator is based on a patient's lean body weight. In typical situations tidal volume is calculated at 10 milliliters (mL) of volume per kilogram (kg) of lean body weight.

Prior to mechanical ventilation the patient should be weighed to set tidal volume appropriately. However, in clinical practice, particularly in emergency situations, it is difficult or impossible to weigh the patient. Lean body weight must be estimated in these situations. In situations where body weight is readily available estimation of lean body weight may still be required since tidal volume is based on a patient's lean body weight and not overall body weight. Errors in the estimation of lean body weight can potentially lead to hypo- (under) or hyper- (over) inflation, the latter condition predisposing to pulmonary barotrauma.

Similarly, the ventilator rate, is in some respects, subjectively estimated based on the skill of the clinician. Since minute ventilation equals tidal volume times ventilator rate, inappropriate selection of ventilator rate, and thus minute ventilation, can occur if ventilator rate is inappropriately set, possibly resulting in hypo- or hyperventilation which, in turn, can lead to respiratory acid-base disturbances and physiologic abnormalities.

Unskilled clinicians with minimal experience in treating patient's with respiratory failure are at greater risk of setting the ventilator inappropriately, resulting in the aforementioned problems. A safer approach is to set tidal volume and ventilator rate based on objective criteria, especially when a ventilator is used by unskilled clinicians.

In a study involving anesthetized, apneic patient's receiving mechanical ventilation it was determined that body length and body surface area are comparable predictors of tidal volume to that of lean body weight. Further, it has been found that body length and surface area provide better predictors of ventilator rate than lean body weight.

Figure 15:
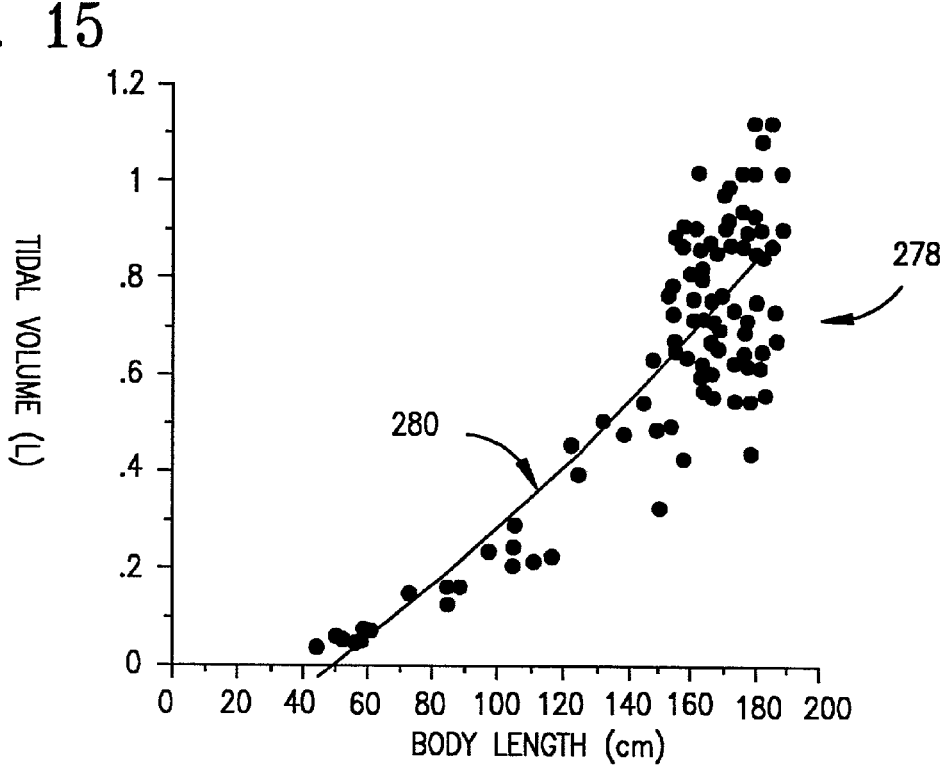
FIG. 15 is a graph depicting the correspondence of tidal volume to body length.

In FIG. 15 there is shown plotted, as a function of body length, data points 278 representing the ideal tidal volume settings for ninety-five patients observed. From these data points, a polynomial regression analysis was performed to determine the polynomial regression line 280 which best fits the data. The results of this analysis are provided below in Table 1.

TABLE 1

Beta Coefficient Table

| Variable | Coefficient | Std. Err. | Std. Coeff. | t-Value | Prob. |
|---|---|---|---|---|---|
| INTERCEPT | −0.21 | | | | |
| x | 3.70E-3 | 2.91E-3 | 0.49 | 1.27 | .2072 |
| $x^2$ | 1.08E-5 | 1.14E-5 | 0.36 | 0.94 | .3498 |

From the data the following polynomial has been developed for estimating tidal volume based on body length (X=body length in centimeters):

$$\text{TIDAL VOLUME } (L) = 0.21 + 0.0037X + 0.0000108X^2$$

Figure 16:
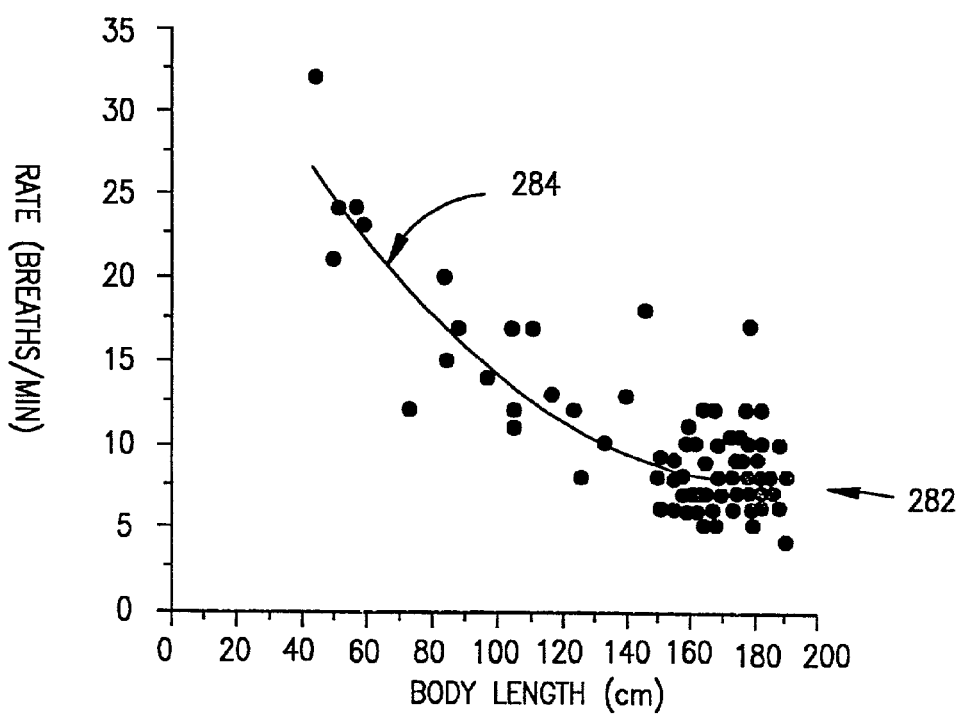
FIG. 16 is a graph depicting the correspondence between breathing frequency and body length.

Similarly, in FIG. 16 there is shown plotted, as a function of body length, data points 282 representing the ideal ventilation rate settings for ninety-five patients observed. The data resulting from the polynomial regression analysis, used to determine the polynomial regression line 284 which best fits the data, is provided below in Table 2.

TABLE 2

Beta Coefficient Table

| Variable | Coefficient | Std. Err. | Std. Coeff. | t-Value | Prob. |
|---|---|---|---|---|---|
| INTERCEPT | 40.59 | | | | |
| x | −0.36 | 0.05 | −2.64 | 7.27 | .0001 |
| $x^2$ | 9.96E-4 | 1.96E-4 | 1.85 | 5.09 | .0001 |

From this data the following polynomial has been developed for estimating ventilator rate based on body length (X=body length in centimeters):

$$\text{RATE (breaths/min)} = 40.59 - 0.36X + 0.000996X^2$$

A correlation prediction analysis was used to determine the physiological predictability of estimating, satisfactorily, the tidal volume and ventilation rate from each of body length, body surface area, and body weight. Good physiological predictability has been found where the $r^2$ value falls within the range 0.64 to 0.81.

The $r^2$ values for tidal volume and ventilation rate as a function of body length were found to be 0.71 and 0.74, respectively. The $r^2$ values for tidal volume and ventilation rate as a function of body surface area were found to be 0.74 and 0.71, respectively. For tidal volume and ventilation rate as a function of body weight the $r^2$ values were found to be 0.73 and 0.62, respectively.

From the $r^2$ calculations it is found that the use of body length or surface area to determine tidal volume gives comparable results to that of using body weight. The $r^2$ values indicate, however, that body length and body surface area provide a better predictor of ventilation rate than body weight.

In the ventilator of the present invention, body length is used to calculate initial settings for the tidal volume and ventilator rate since body length provides a distinct advantage in that it is more readily determined than is body surface area.

When operating in the basic mode, body length is determined and entered into the ventilator by the operator through switches 240, FIG. 12. This information is provided to the software which has programmed therein algorithms for implementing the polynomials for calculating the tidal volume and the ventilation rate from body length, will use this information to determine the initial settings for tidal volume and ventilation rate.

Although the invention has been described in terms of manual entry of the body length, it is contemplated that ventilator devices may be implemented according to the present invention that have mechanisms for automatically determining and entering this information. By way of example, it is contemplated that ultrasonic measuring devices, lasers, built in tape reels connected to an electronic potentiometer, or the like, may be utilized to determine the body length of the patient.

In addition to setting tidal volume and ventilation rate based on body length, limits for ventilatory parameters are based on patient length. With conventional ventilators it is possible for unskilled users to set ventilatory parameters, such as pressure levels in PSV and PCV modes, which are too high for the patient. By incorporating algorithms to determine limits for the ventilatory parameters based upon patient length these potentially dangerous situations can be avoided. Similarly, in the ventilator of the embodiment of FIG. 1 the ventilator control board 222 has programmed therein algorithms for setting the ventilation alarms based on the patient's length.

In providing mechanical ventilation, it is essential that the ventilation parameters are appropriate. A lockout mechanism is provided in the ventilator of the present invention to prevent back-up ventilator subsystem 66, FIG. 2, operation using inappropriate ventilation parameters.

Operation using inappropriate settings could occur where, after being disconnected from gas and electrical supplies, the gas supply is connected to the ventilator prior to the electrical supply being connected. In this scenario if the back-up ventilator parameters set during use on a prior patient remain, the backup ventilator will operate using these parameters.

With the back-up ventilator lockout mechanism, when the user turns off the ventilator, the microprocessor of the ventilator control board will operate the stepper motor 104 to shut off the needle valve 100. If the ventilator is moved and then the gas supply connected prior to the electrical supply being connected, the back-up ventilator will operate but will be unable to supply gas to back-up ventilator output line 102.

A potential also exists that, after an electrical failure occurs, and back-up ventilator operation has occurred, the ventilator will be disconnected prior to reestablishing the electrical supply. In this scenario the primary and back-up ventilator settings remain those for the previous patient.

In the scenario above a lockout mechanism is provided in the form of a verification sequence which must be followed prior to the ventilator switching from back-up mode to primary ventilation mode. This lockout mechanism requires the user to verify that the ventilator is connected to the same patient that it was prior to electrical failure before the ventilator will switch back to primary ventilation mode.

When the ventilator is switched on after electrical supply has been reestablished, the LCD display 236, FIG. 12, and an audible alarm 238 will prompt the user to input, through switches 240, information to establish that the ventilator is connected to the same patient as before the electrical failure. The information is transmitted to the microprocessor of the ventilator control board 222 wherein the data is used to determine if the ventilator may switch back to primary ventilation mode.

If the microprocessor of the ventilator control board 222 determines, through the input information, that the ventilator is no longer connected to the same patient, primary ventilation mode will remain disabled, the BUV will be disabled by turning the flow to 0 and the microprocessor of the ventilator control board 222 will instruct the user to enter the new body length into interface control board 218.

An improvement contained in the ventilator of the present invention is that the rate of rise during pressure support ventilation can be adaptively set. A correspondence between patient work of breathing (WOB) and rate of rise in pressure during pressure support ventilation has been identified.

It has been found that WOB varies inversely with rise in pressure, the faster the rate of rise, the lower the WOB and conversely, the slower the rate of rise the higher the WOB.

Figure 17:
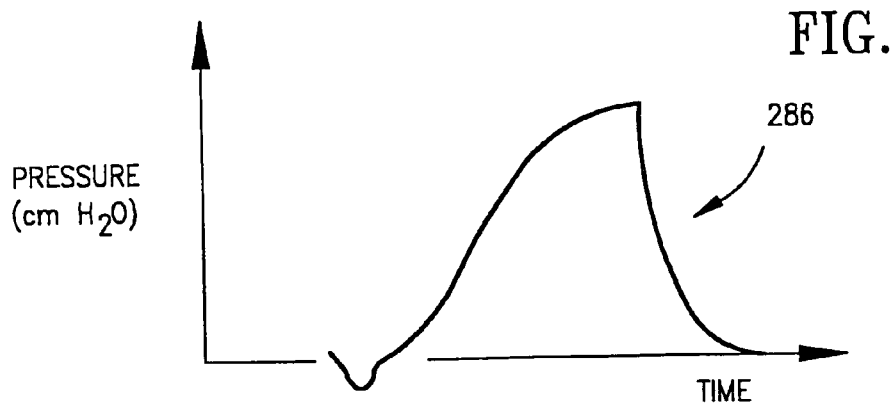
FIG. 17 is a graph depicting a slow rise in pressure during PSV in a ventilator of FIG. 1.
Figure 18:
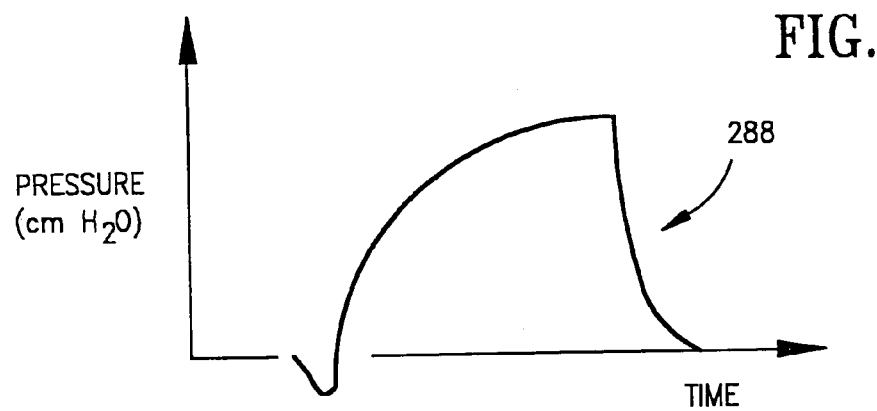
FIG. 18 is a graph depicting an intermediate rise in pressure during PSV in the ventilator of FIG. 1.
Figure 19:
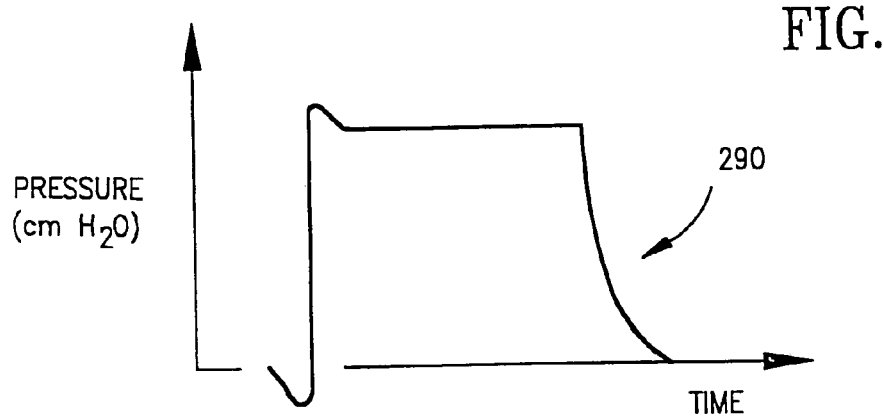
FIG. 19 is a graph depicting a fast rise in pressure in the ventilator of FIG. 1.

As the rate of rise in inspiratory pressure increases from a slow rate of rise 286, FIG. 17, to an intermediate rate of rise 288, FIG. 18, there is a consequent reduction in the WOB. Similarly, when the rate of rise in pressure approaches that of a square wave 290, FIG. 19, the ventilator output better matches the inspiratory pressure resulting in a decreased WOB.

It has been discovered, that the optimal rate of rise in pressure, and thus minimal WOB, is achieved when rate of rise is matched to the pulmonary mechanics of the patient. The ventilator unit of the preferred embodiment of the present invention utilizes this discovery by adaptively setting the rate of rise when PSV mode is activated.

The ventilator evaluates 5 different rates of pressure rise and chooses the rate of rise that results in a square shaped pressure wave form with minimal ringing.

Nothing contained herein should be taken to limit the invention to the use of five of rise. It is anticipated that any number of rates of rise could be utilized in a ventilator unit in accordance with the present invention.

An integral barometric pressure transducer is included in the preferred embodiment of FIG. 1 to detect changes in ambient pressure. As significant changes in pressure from ambient occur the microprocessor on the ventilator control board 222 compensates and increases or decreases the aperture of the PFCV valve 58 to appropriately maintain the selected tidal volume and offset changes due to ambient pressure. For example by using a lookup table or algorithm.

The control software, of the ventilator of FIG. 1, will now be described with reference to FIGS. 20a–20e.

Figure 20A:
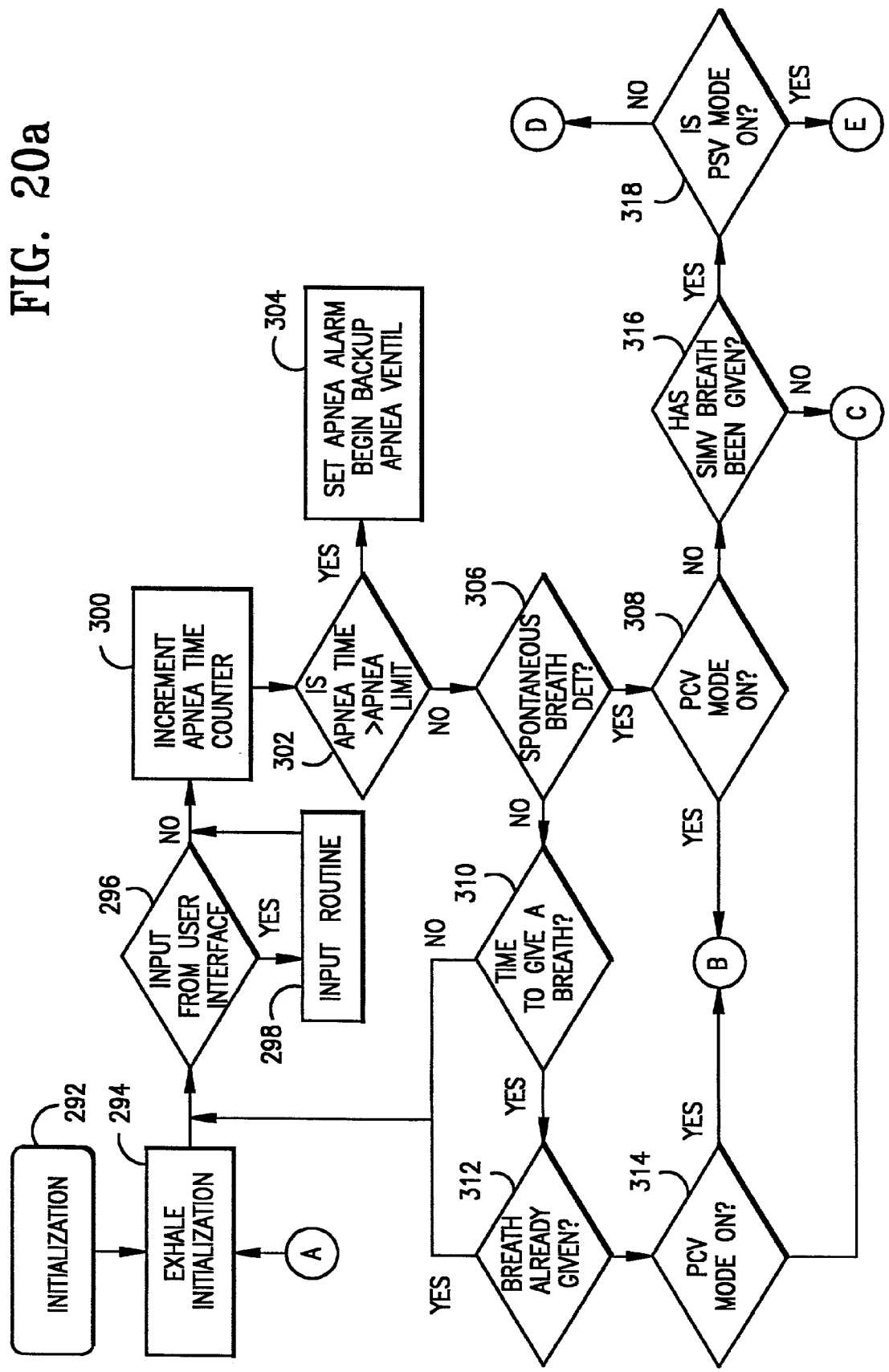
FIGS. 20a–20e are flowcharts depicting the operation of the ventilator of FIG. 1.

Control of the system commences upon power up with the initialization of the ventilator 292, FIG. 20a. During initialization of the ventilator 292 the pressure transducers 48, 84, 160 are zeroed, the BUV needle valve 100 is closed, CPAP is set to zero, the patient's length is accepted and the ventilator parameters are set based on that length.

Following the initialization 292, the ventilator performs an exhale initialization 294 wherein the flow of gas to the primary gas supply line 78, FIG. 2, is shut off and the exhalation valve 126 is opened. During the exhale initialization 294 breath parameters, including peak inspiratory pressure and tidal volume are reset. The apnea timer counter, used to identify potential apneic episodes, is reset during exhale initialization 294. Tests are also performed during exhale initialization 294 for the existence of alarm conditions.

Following exhale initialization 294, the user interface board is polled for new inputs 296. If new inputs are present an input routine 298 is performed wherein the ventilator parameters are set in accordance with the new inputs. Once the new inputs are entered, or if no new inputs exist, the apnea timer counter is incremented 300 and compared against a preselected apnea limit 302.

If the apnea timer counter exceeds the apnea limit an apnea alarm will be sounded and apnea backup ventilation will begin 304. During apnea backup ventilation, forced IMV breaths are provided until the patient begins spontaneous breathing or the ventilator parameters are reset.

If the apnea timer counter does not exceed the apnea limit 302 the ventilator checks for the existence of spontaneous breathing by the patient 306. A set of conditional steps then determines which of the four ventilation types, i.e. PCV, SIMV, CPAP and PSV, to initialize.

Figure 20B:
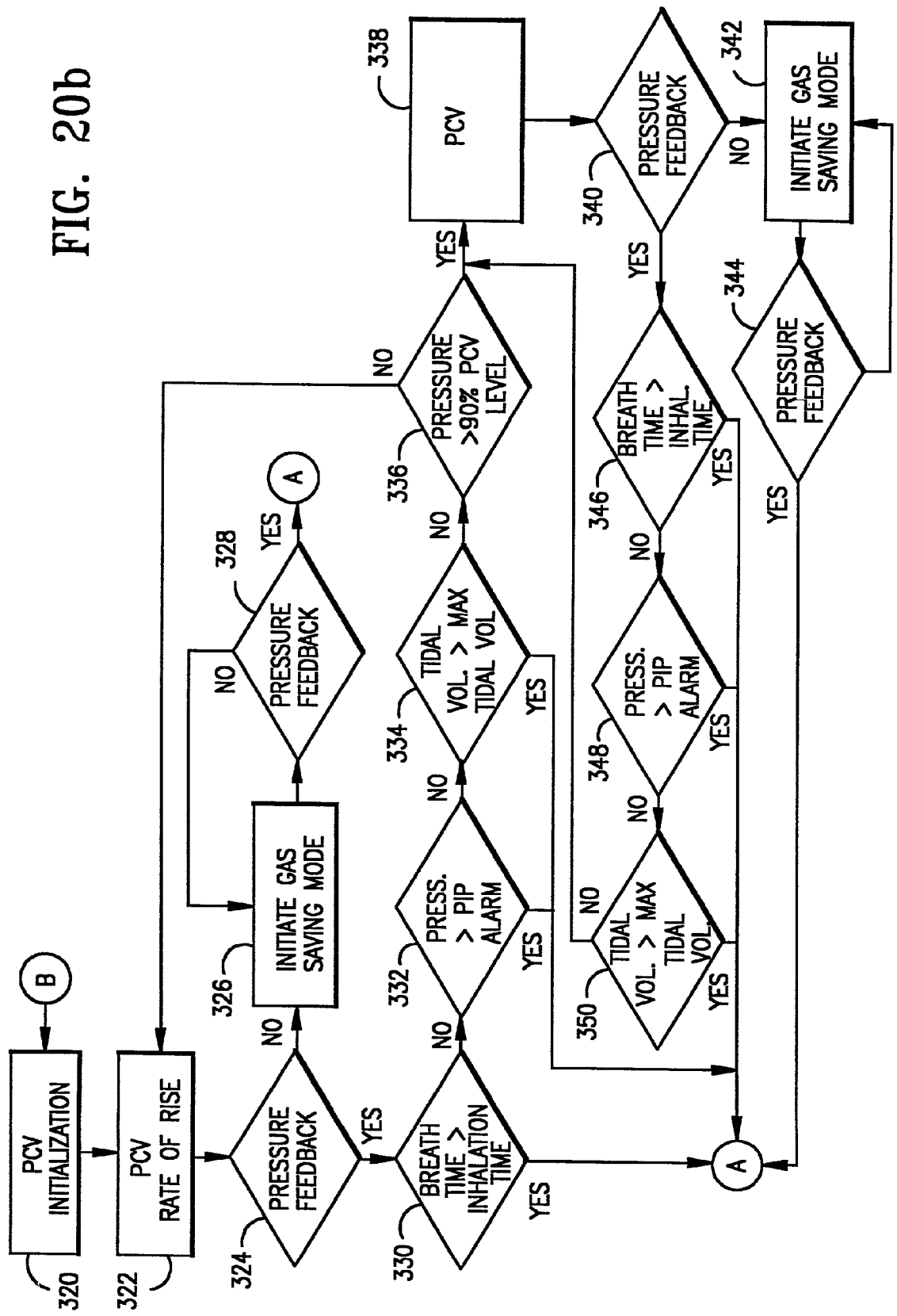

If a spontaneous breath is detected 306 and the PCV mode is on 308, PCV initialization is performed 320, FIG. 20b. Alternatively, if a spontaneous breath has been detected 306, PCV mode is off 308 and a SIMV breath has not been given 316 SIMV initialization is performed 352, FIG. 20c.

Similarly, if no spontaneous breath has been detected 306, it is time to give a breath 310, a breath has not been given 312 and the PCV mode is on 314, PCV initialization is performed 320, FIG. 20b. If no spontaneous breath has been detected 306, it is time to give a breath 310, a breath has not already been given 312 and the PCV mode is off 314, SIMV initialization is performed 352, FIG. 20c. If, however, it is determined that it is not time to give a breath 310 or that a breath has already been given 312 the flow of control will return to checking for new inputs 296.

Figure 20C:
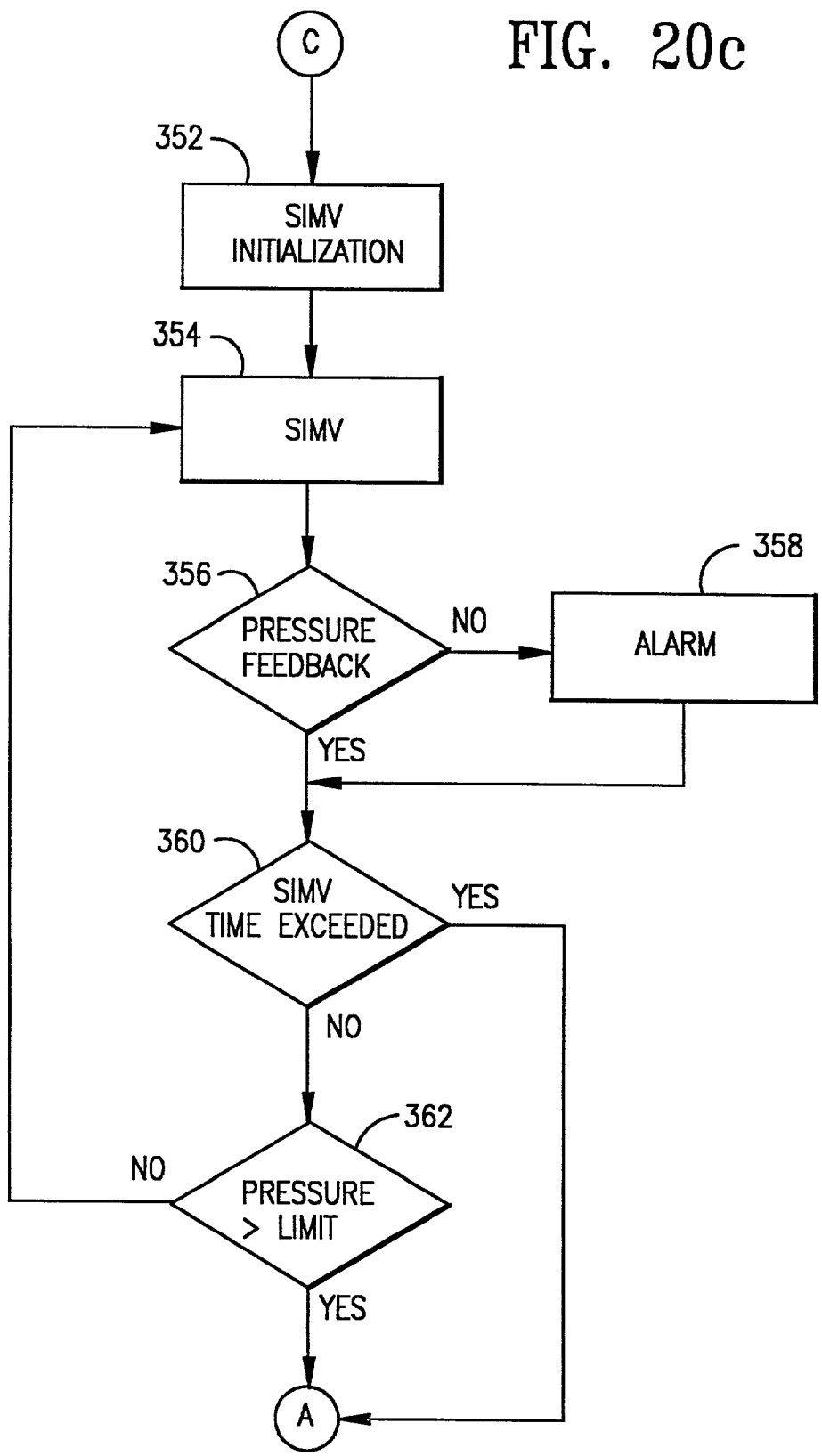
Figure 20D:
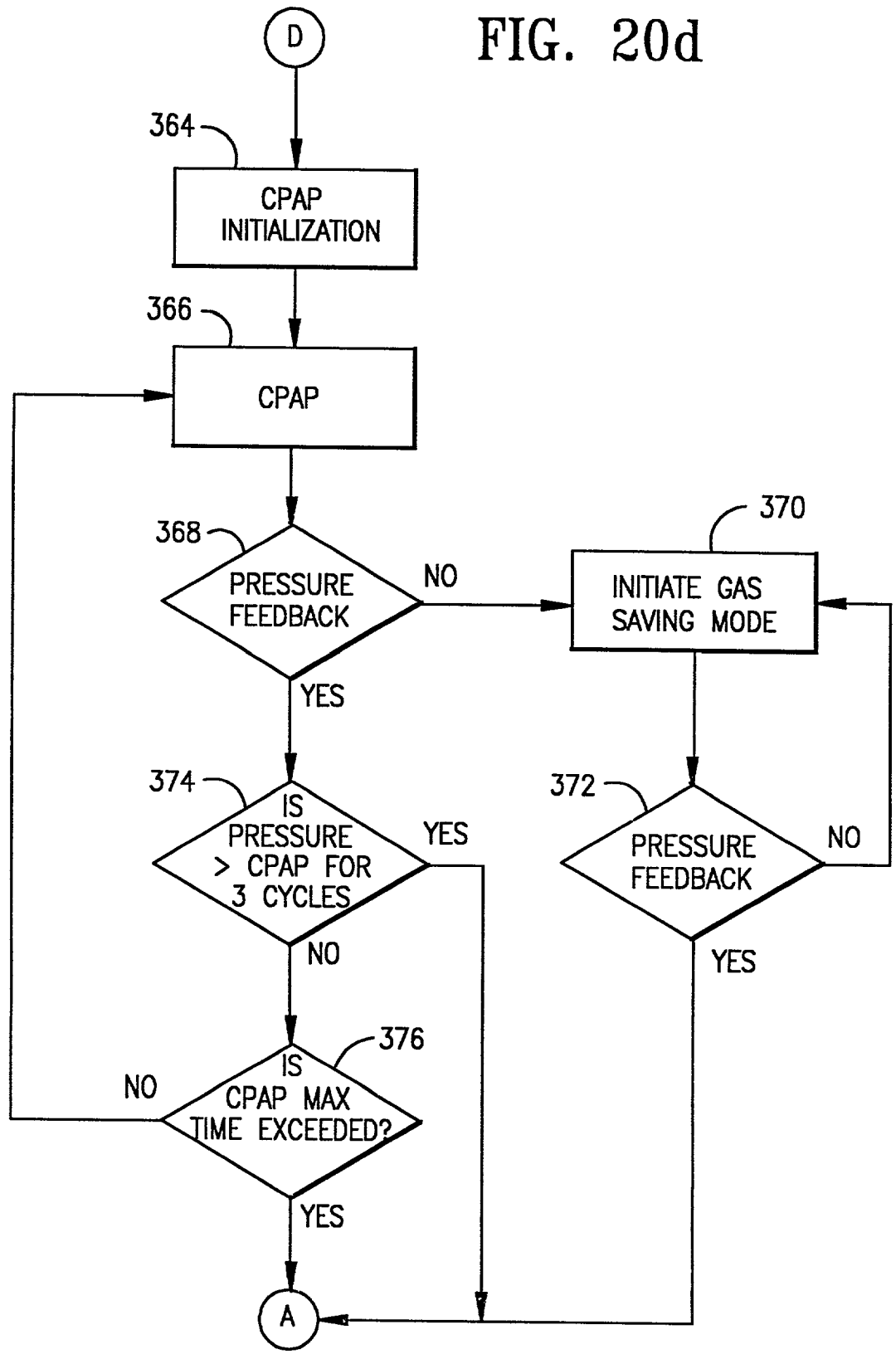

If a spontaneous breath is detected 306, PCV mode is off 308, a SIMV breath has been given 316 and the PSV mode is off 318, CPAP initialization is performed 364, FIG. 20d. Alternatively, if a spontaneous breath has been detected 306, PCV mode is off 308, a SIMV breath has been given 316 and the PSV mode is on 318, PSV initialization is performed 378, FIG. 20e.

During PCV initialization 320, FIG. 20b, the exhalation valve 126, FIG. 2, is closed and the initial flow rate is set. Additionally, since pressure must be controlled during PCV ventilation, the flow rate necessary to maintain the desired pressure is determined and set by a proportional integral derivative (PID) controller. Pressure control is achieved in this manner since the pressure cannot be directly adjusted but instead is adjusted by varying flow rate.

Following the PCV initialization step 320, PCV rate of rise is selected 322. In selecting the appropriate PCV rate of rise, the flow rate is adjusted based on the PID controller to maintain the current pressure rate of rise. Further, the maximum initial flow is calculated.

The pressure sensing line 154 is then checked to determine whether there is pressure in the line 324. If there is no pressure feedback, a disconnect condition is identified, an alarm is triggered and the ventilator initiates gas saving mode operation 326. During the operation of the gas saving mode 326, the pressure in the sensing line is monitored 328 until pressure is detected. When pressure is detected in the pressure sensing line 154 and the ventilator is operating in the gas saving mode 326, exhale initialization will be performed 294.

Following the PCV rate of rise step, 322 if pressure is detected 324, in the pressure sensing line 154, a conditional step is performed to determine if the breath time exceeds the inhalation time 330. If the breath time exceeds the inhalation time 330, exhale initialization 294 is performed. If the breath time does not exceed the inhalation time 330 a next conditional step is performed to determine if the pressure exceeds the peak inspiratory pressure (PIP) 332.

The PIP alarm operates as the high pressure alarm for the ventilator while operating in PCV mode. If the pressure exceeds the PIP alarm 332 exhale initialization 294 is performed. If the PIP alarm is not exceeded a next conditional step is performed to determine if the tidal volume exceeds the maximum allowed tidal volume 334, if so exhale initialization is performed 294.

If the maximum allowed tidal volume is not exceeded, a next conditional step is performed to determine whether the pressure in the pressure sensing line 154 exceeds ninety percent of the PCV level 336. If the pressure does not exceed ninety percent of the PCV level control returns to the PCV rate of rise step 322. If the pressure in the pressure sensing line 154 exceeds ninety percent of the PCV level 336, PCV ventilation 338 is provided.

During PCV ventilation 338 the flow rate is adjusted using the PID to maintain the PCV level. During PCV ventilation, the pressure sensing line 154 is checked for pressure feedback 340. If no pressure is detected, a disconnect situation is detected and the ventilator will initiate gas saving mode operation 342. While operating in gas saving mode 342 the pressure in the pressure sensing line is monitored 344. As long as no pressure is detected in the pressure sensing line 154 the ventilator will remain in gas saving mode 342. When pressure is detected in the pressure sensing line 154 exhale initialization is performed 294.

During PCV ventilation 338, if pressure is detected 340 in the pressure sensing line 154, a conditional loop is performed to determine when to terminate PCV ventilation. Under ordinary conditions, PCV ventilation continues for a preset time and thus, as part of the conditional loop the breath time is monitored to determine if the inhalation time has been exceeded 346. If the inhalation time has been exceeded exhale initialization 294 occurs.

If the inhalation time has not been exceeded the pressure in the pressure sensing line is monitored to ensure that it does not exceed the high pressure PIP alarm 348. If the PIP alarm is exceeded exhale initialization 294 is performed. If the pressure does not exceed the PIP alarm 348 the tidal volume is also checked to ensure that it does not exceed the maximum allowed tidal volume 350. If the maximum allowed tidal volume is exceeded exhale initialization 294 is performed. If the maximum tidal volume has not been exceeded PCV ventilation 338 continues.

Five different rates of rise are provided during the first six PCV breaths, two breaths at each rate of rise. After the first ten PCV breaths the PCV waveform is compared to the target waveform. Following the tenth PCV breath the best rate of rise is determined from the preceding ten PCV overshoot values. This rate of rise will then be used during further PCV ventilation.

During SIMV Initialization 352, FIG. 20c, the exhalation valve 126 is closed and the flow rate is set at a constant value. A SIMV breath is then given 354. During SIMV breaths, the pressure in the pressure sensing line 154 is checked 356. If no pressure exists an alarm is triggered 358 and the ventilator continues providing SIMV ventilation.

During SIMV ventilation 354, the ventilation time is checked to ensure that the SIMV time has not been exceeded 360. Additionally, the pressure in the pressure sensing line is checked to ensure the limit has not been exceeded 362. If neither the SIMV time or pressure limit have been exceeded SIMV ventilation 354 will continue. If either the SIMV time or pressure limit have been exceeded exhalation initialization 294 will be performed.

During CPAP initialization 364, FIG. 20d, the apnea alarm is reset, the PID controller is initialized, and the initial flow is set. During CPAP ventilation the exhalation valve 126 is charged to the CPAP level. Therefore, to minimize gas escaping out of the exhalation valve 126, the target pressure is set during CPAP initialization 364 to the CPAP setting minus 0.5 cm of water.

Following this CPAP initialization step 364, CPAP is then provided 366. During CPAP 366 the flow rate is continually adjusted to maintain the CPAP pressure. The pressure in the pressure sensing line 154 is also monitored 368 during CPAP ventilation 366. If no pressure in the pressure sensing line 154 is detected a disconnect condition is identified and the ventilator will begin operating in the gas saving mode 370.

The ventilator will continue operating in the gas saving mode 370 until pressure is detected 372 in the pressure sensing line 154. When pressure is detected exhale initialization 294 is performed.

During CPAP ventilation 366, if pressure in the pressure sensing line 154 is detected 368, the pressure is monitored for three cycles 374 to see if the pressure exceeds the CPAP pressure. If the pressure does not exceed the CPAP pressure for three cycles and the maximum CPAP time has not been exceeded 376, CPAP continues to be provided 366. Alternatively, if the pressure exceeds the CPAP for three cycles 374 or if the maximum CPAP time has been exceeded 376 exhale initialization 294 is performed.

Figure 20E:
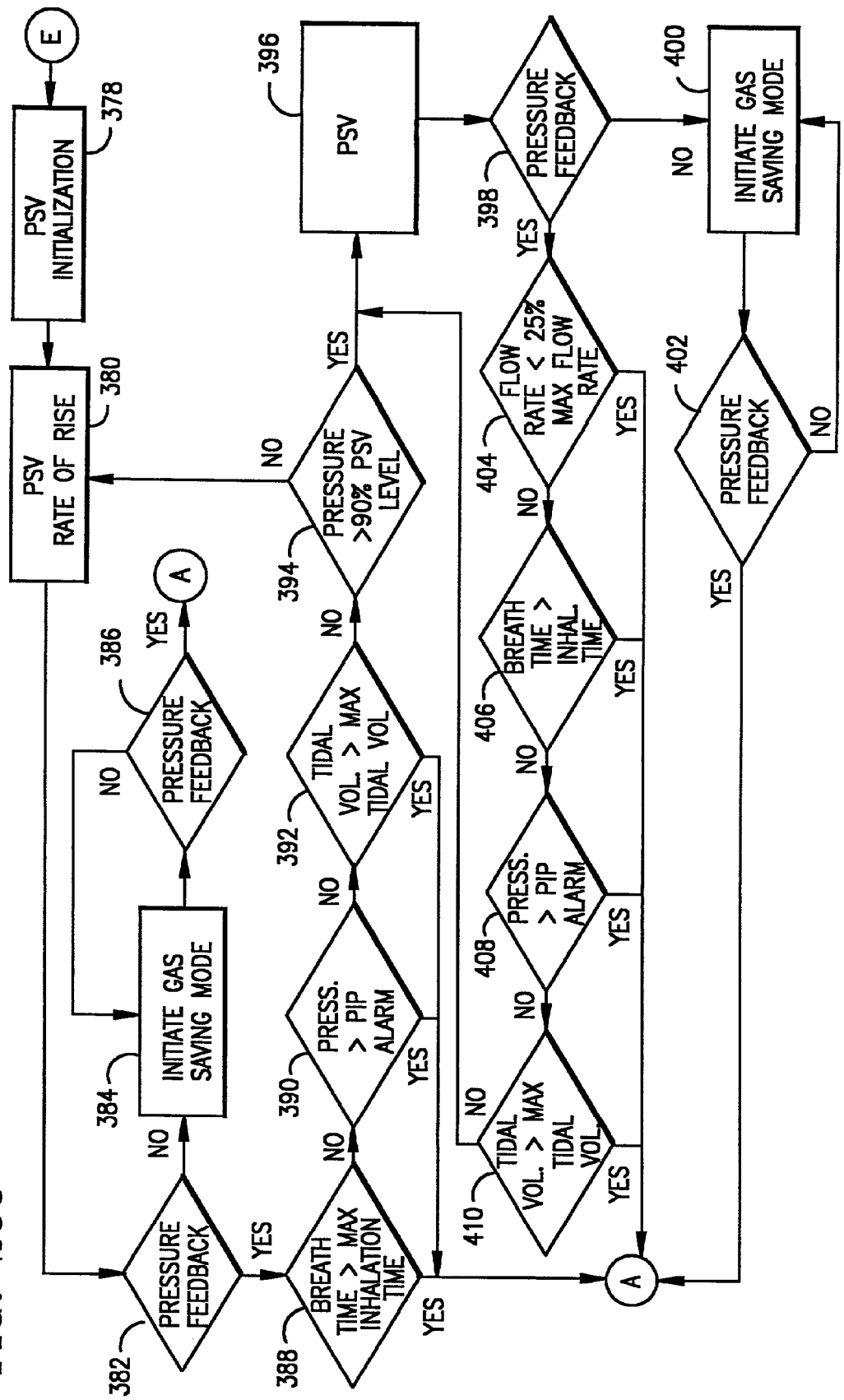

During PSV initialization 378, FIG. 20e, the exhalation valve 126 is closed, the initial flow rate is set and the PID value is calculated. Following PSV initialization 378, the PSV rate of rise is controlled 380. In selecting the appropriate PSV rate of rise, the flow rate is adjusted based on the PID to maintain the pressure rate of rise. Further, the maximum initial flow is calculated.

The pressure sensing line 154 is then checked to determine whether there is pressure in the line 382. If there is no pressure feedback, a disconnect condition is identified and the ventilator will initiate gas saving mode operation 384. During operation in gas saving mode 384, the pressure in the sensing line is monitored 386 until pressure is detected. When pressure is detected in the pressure sensing line 154 and the ventilator is operating in the gas saving mode 384, exhale initialization will be performed 294.

Following the PSV rate of rise step 380 if pressure is detected 382 in the pressure sensing line 154, a conditional step is performed to determine if the breath time exceeds the maximum inhalation time 388. If the breath time exceeds the maximum inhalation time 388 exhale initialization 294 is performed. If the breath time does not exceed the maximum inhalation time 388 a next conditional step is performed to determine if the pressure exceeds the peak inspiratory pressure (PIP) 390.

The PIP alarm operates as the high pressure alarm for the ventilator while operating in PSV mode. If the pressure exceeds the PIP alarm 390 exhale initialization 292 is performed. If the PIP alarm is not exceeded a next conditional step is performed to determine if the tidal volume exceeds the maximum allowed tidal volume 392, if so exhale initialization is performed 294.

If the maximum allowed tidal volume is not exceeded a next conditional step is performed to determine if the pressure in the pressure sensing line 154 exceeds ninety percent of the PCV level 394. If the pressure does not exceed ninety percent of the PSV level control returns to the PSV rate of rise step 380. If the pressure in the pressure sensing line 154 exceeds ninety percent of the PSV level 394 PSV ventilation 396 is provided.

During PSV ventilation 396 the flow rate is adjusted using the PID to maintain the PSV level. After each PSV breath the pressure sensing line 154 is checked for pressure feedback 398. If no pressure is detected a disconnect situation is detected and the ventilator will initiate gas saving mode operation 400. During the gas saving mode operation 400 the pressure in the pressure sensing line is monitored 402. As long as no pressure in the pressure sensing line is detected the ventilator will remain in gas saving mode 400. When pressure is detected 402 in the pressure sensing line 154 exhale initialization is performed 294.

During PSV ventilation 396, if pressure is detected 398 in the pressure sensing line 154, a conditional loop is performed to determine when to stop PSV ventilation. Under ordinary conditions, PSV ventilation continues to a preset pressure and thus, as part of the conditional loop the flow rate is monitored to determine when it becomes less than twenty-five percent of the maximum flow rate 404. When the flow rate drops below twenty-five percent of the maximum flow rate exhale initialization 294 is performed.

If the flow rate has not dropped below twenty-five percent of the maximum-flow rate 404 the breath time is checked to ensure that it does not exceed the maximum inhalation time 406. If the breath time exceeds the maximum inhalation time exhalation initialization 294 is performed. If the breath time does not exceed the maximum inhalation time 406 the pressure sensing line is monitored to ensure that the pressure does not exceed the high pressure PIP alarm 408. If the PIP alarm is exceeded exhale initialization 294 is performed.

If the pressure does not exceed the PIP alarm the tidal volume is also checked to ensure that it does not exceed the maximum allowed tidal volume 410. If the maximum allowed tidal volume is exceeded exhale initialization 294 is performed. If the maximum tidal volume has not been exceeded PSV ventilation 400 continues.

Five different rates of rise are provided during the first ten PSV breaths, two breaths at each rate of rise. After the first ten PSV breaths the PSV waveform is compared to the target waveform. Following the tenth PSV breath the best rate of rise is determined from the pressure profile. This rate of rise will then be used during further PSV ventilation.

Although described above in the context of a transport ventilator, it is anticipated that each of the features described hereinabove would have equal utility if incorporated in other ventilation devices. The above description and drawings are only illustrative of preferred embodiments which achieve the objects, features and advantages of the present invention, and it is not intended that the present invention be limited thereto. Any modification of the present invention which comes within the spirit and scope of the following claims is considered part of the present invention.

The invention claimed is:

1. A method of operating a ventilator to provide pressure support ventilation dependent on a patient's breathing profile, comprising the steps of:
   providing a ventilator having a mechanism for adaptively setting a rate of rise in airway pressure during pressure support ventilation;
   providing a first ventilated breath with a first rate of rise of inspiratory pressure;
   providing a second ventilated breath with a second rate of rise of inspiratory pressure;
   automatically evaluating airway pressure during each of said ventilated breaths;
   automatically selecting the rate of rise in airway pressure having a short period of rise time that provides a square shaped pressure waveform based on the evaluation of said airway pressure of said ventilated breaths; and
   automatically providing ventilation using said selected rate of rise.

2. The method of claim 1, wherein said selected rate of rise provides a square shaped pressure waveform with minimal ringing.

3. The method of claim 1, wherein said rate of rise is selected adaptively by evaluating a plurality of rates of rise.

* * * * *